US009649212B2

(12) United States Patent
Fargahi

(10) Patent No.: US 9,649,212 B2
(45) Date of Patent: May 16, 2017

(54) RELEASE DEVICE FOR RELEASING A MEDICAL IMPLANT FROM A CATHETER AND CATHETER COMPRISING A RELEASE DEVICE

(71) Applicant: BIOTRONIK AG, Buelach (CH)

(72) Inventor: Amir Fargahi, Buelach (CH)

(73) Assignee: BIOTRONIK AG, Buelach (CH)

( * ) Notice: Subject to any disclaimer, the term of this patent is extended or adjusted under 35 U.S.C. 154(b) by 454 days.

(21) Appl. No.: 13/687,393

(22) Filed: Nov. 28, 2012

(65) Prior Publication Data

US 2014/0067037 A1  Mar. 6, 2014

Related U.S. Application Data

(60) Provisional application No. 61/694,781, filed on Aug. 30, 2012.

(51) Int. Cl.
*A61F 2/95* (2013.01)
*A61F 2/966* (2013.01)
A61F 2/24 (2006.01)

(52) U.S. Cl.
CPC .............. *A61F 2/95* (2013.01); *A61F 2/2439* (2013.01); *A61F 2/966* (2013.01); *A61F 2/2436* (2013.01); *A61F 2002/9665* (2013.01)

(58) Field of Classification Search
CPC .. A61F 2/92; A61F 2/962; A61F 2/966; A61F 2002/9665
USPC ...................... 623/1.11, 1.12, 2.11
See application file for complete search history.

(56) References Cited

U.S. PATENT DOCUMENTS

| 7,258,696 | B2* | 8/2007 | Rabkin et al. ............... 623/1.11 |
| 7,611,528 | B2* | 11/2009 | Goodson et al. ............ 623/1.11 |
| 2003/0212410 | A1 | 11/2003 | Stenzel et al. |
| 2011/0264191 | A1* | 10/2011 | Rothstein ..................... 623/1.11 |

(Continued)

FOREIGN PATENT DOCUMENTS

| DE | 102010053111 A1 | 6/2010 |
| EP | 1637176 A1 | 3/2006 |
| WO | 9951166 | 10/1999 |

OTHER PUBLICATIONS

European Search Report for 12190720.8.
English abstract of DE_10 2010 053 111_A1.

*Primary Examiner* — Diane Yabut
(74) *Attorney, Agent, or Firm* — Wagenknecht IP Law Group PC

(57) ABSTRACT

A release device for releasing a medical implant from an insertion device, having an indirect or direct clamping body for clamping the implant in the insertion device, the clamping device having a proximal end, and having a distal end, wherein the clamping body has at least one web, at least one extension and at least two clamping surface regions, wherein the extension is oriented substantially in the radial direction of the clamping body, and wherein the at least two clamping surface regions are substantially pointing toward one another and are aligned substantially parallel to one another, wherein the at least one web or the at least one extension has at least one of the two clamping surface regions, and wherein the at least two clamping surface regions and/or the at least one extension connect/connects to at least one region of the implant in the clamped state.

13 Claims, 13 Drawing Sheets

(56) References Cited

U.S. PATENT DOCUMENTS

2011/0264203 A1* 10/2011 Dwork ................. A61F 2/2418
623/2.11

* cited by examiner

RELEASE DEVICE FOR RELEASING A MEDICAL IMPLANT FROM A CATHETER AND CATHETER COMPRISING A RELEASE DEVICE

CROSS REFERENCE TO RELATED APPLICATIONS

This application claims benefit of priority to U.S. provisional patent application Ser. No. 61/694,781, filed Aug. 30, 2012; the contents of which are herein incorporated by reference in their entirety.

TECHNICAL FIELD

The invention relates to a release device for releasing a medical implant from a catheter and to a catheter comprising a release device for releasing a medical implant for implantation in an animal and/or human body.

BACKGROUND

In the field of medicine, implants are often used that are introduced into an animal and/or human body either permanently or at least for a relatively long period of time in order to carry out replacement functions. For example, these implants could include heart pacemakers, brain pacemakers for Parkinson's patients, cardiac implants, cochlear implants, retina implants, dental implants, implants for joint replacement, vessel prostheses or stents.

Implants are connected to catheters before insertion into the body and have to be fastened such that they can be positioned precisely at the site for use without complication and can be released in a defined manner by the catheter. To this end, it is known for example to equip the implant with eyelets that cooperate with hooks on the catheter and thus fasten the implant to the catheter. For example, it is known from EP 1 389 977 B1 to provide hooks on an insertion device, said hooks pointing radially toward the inner axis and engaging in structures of the implant to fasten the implant to the insertion device.

The object of the invention is to disclose a release device with which an implant can be connected to an insertion device in a simple and user-friendly manner and with which an implant can be released in a highly precise and selective manner.

A further object can be considered that of providing a corresponding insertion device.

SUMMARY

The object is achieved in accordance with the invention by the features of the release and insertion devices provided herein. Advantageous embodiments and advantages of the invention will emerge from the description.

A release device for releasing a medical implant from an insertion device is proposed, with which the implant can be released by a relative movement between a first and a second insertion element. The release device includes an indirect and/or direct clamping body for clamping the implant in the insertion device, the clamping body including a proximal end, which is remote from a distal end of the insertion device during use, and including a distal end, which faces the distal end of the insertion device during use, wherein the clamping body has at least one web, at least one extension and at least two clamping surface regions, wherein the extension can be arranged so as to be oriented substantially in the radial direction relative to an inner axis of the clamping body, and wherein the at least two clamping surface regions are arranged so as to be substantially pointing toward one another and are aligned substantially parallel to one another, wherein the at least one web or the at least one extension includes at least one of the two clamping surface regions, and wherein the at least two clamping surface regions and/or the at least one extension non-positively and/or positively connect/connects to at least one region of the implant in the clamped state.

As a result of the embodiment according to the invention, a release device can be provided in which the implant is held securely or is fastened securely on an insertion element, such as an inner shaft for example, of the insertion device. The clamping body further allows a compact and simple design of the release device. In addition, a simple concept for clamping or holding and for releasing the implant is thus implemented. As a result of the clamping body, an undesired movement of the implant, for example what is known as "jumping", when the implant is fed to a site of implantation and/or when the implant is released can be prevented. Furthermore, the release device has simple handling and assembly of the implant on the insertion device, for example a catheter, in the preparation lab. Release of the implant is also reliable and quick. In addition, a risk of deformation of the implant and of a resultant jamming of the release device, as occurs in prior art devices that function with hooks and eyelets, can be eliminated. Such a clamping body is also particularly patient-friendly, since a risk of hooks and eyelets shearing through the implant and of resultant detached particles being located in the body of the patient, as may occur in prior art devices, is prevented. The partially released implant can particularly advantageously be repositioned by means of the embodiments according to the invention. This is particularly the case since the clamping body can generate a large clamping or holding force. In addition, a function test of the implant can be carried out and, in the case of defect, the faulty implant can be removed.

In this context a "clamping body" is understood to mean a body that holds another element, in particular the implant, on a component of the insertion device, in particular an insertion element or the inner shaft, in a fixed position by means of a clamping effect and/or a non-positive fit. In this case, the clamping body may provide the clamping effect itself and/or provide the clamping effect directly and can thus be considered and/or referred to as a direct clamping body. For example, this could be a cylindrical element and/or a holder or implant holder, which holds or clamps the at least one region of the implant in the insertion device. Alternatively and/or additionally, the clamping body may cooperate with at least one further element, in particular of the insertion device, such as an insertion element or the inner shaft and/or an outer shaft of the insertion device and/or a stopper, and may provide the clamping effect indirectly. Such a clamping body can thus be considered and/or referred to as an indirect clamping body. In addition and preferably, the clamping body, in particular the indirect clamping body, may have a holding effect that is separate from the clamping effect and is produced for example by a form fit between at least part of the clamping body and the at least one region of the implant. In this instance, it would also be conceivable to form the clamping body with an (additional) special material property. In this case, a "clamped state" and/or a "held state" is/are a state in which the implant is held captively in the insertion device. In particular, the clamped state constitutes a radial fixing and the held state constitutes an axial fixing of the at least one region of the implant. A region of the implant may be an end of the implant and, when assembled in the release device, may be a proximal or distal end of the implant. In principle however, any other region of the implant could be connectable, holdable and/or fixable non-positively and/or positively with parts of the clamping body.

In this context, a "web" of the clamping body is to be understood preferably in this instance to mean a structure that can provide an indirect and/or direct holding and/or clamping effect and/or provide a non-positive fit to hold the implant in the insertion device. In particular, the indirect holding effect can be provided in this instance by the indirect clamping body, and the direct holding effect can be provided by a direct interaction of the at least one web with the at least one region of the implant. In the latter case, this is provided in particular by the at least one extension (see below).

An "extension" is understood to mean a structure, such as a lip, a bead, a ring segment and/or a bulge, that extends in a bead-like manner in a substantially radial direction relative to the inner axis of the clamping body. The phrase "can be arranged so as to be oriented substantially in the radial direction relative to an inner axis of the clamping body" is to be understood to mean that the at least one extension can be arranged substantially perpendicular to the inner axis and/or is arranged in the clamped and/or held state. In this case, "substantially in the radial direction and/or perpendicular" are to be understood to mean that a deviation of the direction of the at least one extension from the direction of the inner axis of up to 30° to the perpendicular arrangement thereof is to be understood as "perpendicular". A height of the at least one extension in the radial direction may correspond substantially to a width of the at least one extension in a direction of extension, such as a peripheral direction (see below for further details). In principle, the at least one extension could also have a structure extending substantially linearly in the radial direction or direction of extension, that is to say a structure in which the height is greater than the width or vice versa. The at least one extension may have any desired cross-sectional form, for example polygonal, triangular or rectangular, square, barbell shaped, oval or round.

In addition, in this context a "clamping surface region" is to be understood to mean a portion of a surface of the clamping body and/or of the at least one web and/or the at least one extension that, due to the interaction thereof and or contact thereof with another element, region, area, surface and/or outer face of an element, such as an insertion element and/or in particular the implant, holds the other element, such as the implant, in its position. The clamping force or holding force and/or the non-positive fit of the clamping body is thus transferred onto the implant by means of the clamping surface region. The phrase "arranged so as to be substantially pointing toward one another" is to be understood to mean that the clamping surface regions are substantially radially opposed, wherein "substantially radially opposed" defines that at least 5%, advantageously at least 20%, and more preferably at least 50%, of one clamping surface region is arranged radially opposite the other clamping surface region. In addition, "aligned substantially parallel to one another" is to be understood to mean that a deviation in the direction of one clamping surface region relative to the other clamping surface region of up to 30° to the parallel arrangement thereof is to be understood as "parallel". The at least one clamping surface region of the at least one web and/or the at least one extension preferably lies at a radially inner end of the at least one web and/or at least one extension.

A particularly stable and reliable design of the clamping body can be provided if the at least two clamping surface regions are formed on the same component or are both formed on the at least one web and/or at least one extension. In other words, the at least two clamping surface regions are designed integrally. In this case, "integrally" is to be understood to mean that a first clamping surface region and a second clamping surface region can only be separated from one another with a loss of function of at least one of the clamping surface regions.

In an alternative preferred embodiment, the at least two clamping surface regions are both formed on identical components of the clamping body, that is to say both clamping surface regions are arranged and/or formed either on at least two webs or two extensions, whereby each can be adapted individually to different conditions of the implant, such as pitch, curvature, etc. or to deviating functions, such as gradual or site-specific release of the region of the implant, or the like. In principle however, the arrangement of one clamping surface region on a web and of the other clamping surface region on one of the extensions would also be conceivable.

The at least two clamping surface regions preferably extend around one of the insertion elements, in particular the inner insertion element, in a direction of extension along a contour of the clamping body, such as preferably in the peripheral direction. As a result of this embodiment, the clamping body may advantageously be adapted to a shape of the implant, which is round in particular, thus enabling an exact connection between the clamping body and the regions of the implant.

In a preferred embodiment of the release device with a direct clamping body for clamping the implant in the insertion device, the at least one web preferably includes the at least one clamping surface region. This at least one web provides an indirect non-positive fit to hold the at least one region of the implant in the insertion device with the aid of the direct clamping body. In this case, based on the at least one region of the implant, the release device additionally has an indirect clamping body. This indirect clamping body may be formed in particular in the form of the outer insertion element, which clamps the direct clamping body (directly in this case based on the at least one region of the implant) by pressing against the clamping surface region of the at least one web. In accordance with this embodiment, the holding function is assisted additionally and preferably by a positive fit between the at least one extension and the at least one region of the implant.

In an alternative embodiment of the release device with an indirect clamping body for clamping the implant in the insertion device, the at least one extension preferably includes the at least one clamping surface region. In this case, the indirect clamping body may be formed in particular in the form of the outer insertion element, which clamps the at least one region of the implant by pressing against the clamping surface region of the at least one extension. This at least one extension provides a direct non-positive fit to hold or clamp the at least one region of the implant in the insertion device, since the at least two clamping surface regions clamp therebetween the at least one region of the implant in the clamped state.

Accordingly, it may be preferable either for the at least two clamping surface regions, in particular of the at least one extension, to non-positively connect to the at least one region of the implant in the clamped state, or for the at least one extension to positively connect to at least one region of the implant in the clamped state and/or in the held state.

The at least one web and/or the at lest one extension can advantageously and preferably be designed, for example to boost the clamping or holding force, such that it exerts a clamping force, together with the insertion element, onto the (in particular indirect) clamping body and/or the at least one region of the implant. For example, this can be realized via a spring property of the at least one web and/or the at least one extension. This can be implemented with simple design by forming the at least one extension and/or the at least one web resiliently. In addition, the positive fit between the at least one extension and the at least one region of the implant can thus also be released quickly and reliably by means of the resilient embodiment.

In addition, it may be advantageous if the at least one web can be arranged relative to the inner axis of the clamping body at an angle of substantially 30°. An arrangement of the at least one web is hereby selected such that this can be easily overcome, for example with establishment of the clamping effect or of a clamping position of the clamping body in the clamped state. An "angle of substantially 30°" is understood to mean an angle of 30°±15°. This arrangement is adopted by the at least one web, in particular in a neutral position, that is to say the released clamping position of the indirect clamping body or of the outer insertion element. The at least one extension is further advantageously arranged on the at least one web at an angle of substantially 70°. The at least one extension may thus be moved, preferably together with the at least one web, in particular by a movement of the at least one web. An "angle of substantially 70°" is understood to mean an angle of 70°±30°. The at least one extension may preferably be arranged at an axial end of the at least one web. In addition, the at least one extension may be connected to the at least one web on the basis of any type of fastening considered usable by a person skilled in that art, such as a positive fit, an integral bond, and/or a non-positive fit. The at least one extension is preferably molded on the at least one web and/or is formed integrally therewith, wherein "integrally" is understood to mean that the at least one extension and the at least one web are formed by the same component and/or from a cast part and/or can only be separated from one another with a loss of function of at least one of the elements.

The at least one web can be arranged and/or molded on a fastening element. This end preferably lies axially opposite the end at which the at least one extension is arranged. This fastening means may also one of the clamping surface regions. Furthermore, the fastening element can be used to fasten the at least one web and/or the at least one extension to one another and/or to one of the insertion elements. Furthermore, the fastening element can be formed by any element considered expedient by a person skilled in the art, such as a ring, a tube, a cylinder and a bushing. In the case of a bushing, a cylinder jacket of the bushing extends preferably substantially parallel to the inner insertion element. "The phrase "substantially parallel" is to be understood to mean that a deviation of the direction of the jacket from the direction of the inner insertion element of up to 30° to the parallel arrangement thereof is to be understood as "parallel". With regard to the definition for "substantially parallel", reference is in turn made to the definition in the text above.

In the clamped state, interaction between a holding force of an insertion element (in particular the outer insertion element) or the indirect clamping body (based on the at least one region of the implant) and a holding force of the at least one web of the clamping body advantageously holds the implant in position, whereby the implant is prevented from slipping out from the release device. In the embodiment with the direct clamping body or the, for example cylindrical, (implant) holder, a risk of the at least one region of the implant slipping out from the direct clamping body is meanwhile minimized or preferably completely eliminated by an interaction between a holding force of the at least one region of the implant and a holding force of the direct clamping body. It is also advantageous if the at least one web of the clamping body can be opened due to a self-expended force. Due to the automatic opening, a high level of precision can be achieved when the implant is positioned, instead of using hooks and eyelets as in the prior art.

With the embodiment of the clamping body as a direct clamping body in the form of a holder for the at least one region of the implant in combination with a holding and/or clamping of the at least one region of the implant on the basis of the at least one web and/or the at least one extension of the clamping body, the clamping body can be understood as a hasp holder, operating by the principle of a hasp. In this instance, the positive fit between the at least one extension and the at least one region of the implant due to the spring property of the at least one web can be released easily and quickly.

In accordance with a preferred embodiment, the clamping body has a holding position in the clamped state, in particular in the radial clamped state of the at least one region of the implant. This holding position preferably axially fixes the at least one region of the implant in the clamping body or the release device and/or can advantageously be provided by the positive fit between the at least one extension and the at least one region of the implant. By contrast, when the holding position is released, or when the positive fit is released, the clamping body advantageously has an (axial) neutral position. In this case the clamping body is movable into the neutral position by a resilience of the at least one web and/or of the at least one extension so as to release the at least one region of the implant. This allows the release device to be operated easily in a controlled manner. Furthermore, the clamping body can thus be designed such that the holding force dissipates automatically due to a property of the clamping body or the at least one extension or the at least one web, or such that the clamping body can be opened automatically to release the region of the implant. A separate release means for releasing the holding force and/or for opening the clamping body or the hasp can thus be omitted, whereby components, space, assembly effort and costs can be saved. In the neutral position the implant can also adopt an intermediate position for the complete release thereof, in which only a region of the implant is released for example.

Alternatively and/or in addition, the clamping body may have a clamping position in the clamped state. In the clamping position the at least one region of the implant is preferably radially fixed. When the clamping position is released, the clamping body advantageously adopts a (radial) neutral position. In this case the at least one region of the implant is fixed neither radially nor axially in the release device. In a preferred embodiment the clamping body can be moved by a resilience of the at least one web and/or of the at least one extension into the neutral position to release the at least one region of the implant. In this case too, the clamping body can thus be designed such that the clamping force dissipates automatically due to a property of the clamping body or the at least one extension or the at least one web, or such that the clamping body can be opened automatically to release the region of the implant. As a result, it is also possible in this instance to dispense with a separate release means for releasing the clamping force.

The clamping body advantageously includes at least one receptacle for the at least one region of the implant. The implant can thus be held securely and reliably in the release device. In this context, a "receptacle" is to be understood to mean any structure suitable for a person skilled in the art, for example a recess, an indentation, an opening, a depression, a gap or a slit, which is designed and/or prepared and/or shaped to receive at least the at least one region of the implant. In this case, an edge of the receptacle, such as a lateral surface of the receptacle, provides the clamping effect of the clamping body. So as to form a receptacle of the at least one region of the implant in an unhindered and simple manner, the dimensions of the receptacle, such as a height, a width and/or a depth, have to be adapted to the conditions of the at least one region of the implant, such as a thickness, a contour and/or a shape, etc. A person skilled in the art will do this automatically on the basis of his knowledge in the art.

In an advantageous embodiment, the at least one receptacle includes at least one slit to receive the at least one region of the implant, whereby the design of the receptacle can be adapted easily to a shape of the at least one region of the implant. Reliable reception and secure holding of the at least one region of the implant can be provided if the at least one receptacle or the at least one slit extends at least along part of an edge of the clamping body. In this context, an edge is to be understood to mean an outline, an outer contour, outer face and/or, if the clamping body is round, a circumference. If the clamping body is cylindrical, the at least one receptacle or the at least one slit preferably extends along part of a circumference of the clamping body. Round implants, such as stents, can thus be held or clamped particularly comfortably in the release device. A particularly effective and also loadable connection between the at least one region of the implant and the clamping body can be achieved if the at least one receptacle or the at least one slit extends completely along the edge and in particular the periphery of the clamping body.

The at least one receptacle preferably has at least one separating structure, which divides the at least one receptacle into at least two receptacle sectors. Different parts or regions of the at least one receptacle can thus advantageously be adapted to specific conditions of the at least one region of the implant, such as a thickness, a width, a depth, a curvature, etc. A separating structure is to be understood in this instance to mean any structure that divides the at least one seat, such as a rib, a web, a hole, etc. It may additionally be advantageous if the at least one separating structure, at least in the intended insertion state, fixes the at least one region of the implant in the at least one receptacle in a direction along the edge and/or the periphery of the clamping body. Displacement of the implant along the edge or in the peripheral direction is thus prevented. In this case, the intended end state is to be understood in particular to mean the state in which the at least one region of the implant is introduced into the at least one receptacle, where it is preferably held, in particular in a manner secured against rotation. This may therefore also be an assembled state of the implant in the release device.

A width of one of the at least two receptacle sectors along the edge of the clamping body and/or in the peripheral direction is adapted in particular to the conditions of the at least one region of the implant, such as a shape along a contour and/or a periphery of the implant. If the implant is a stent for example having a lattice structure formed from rhombic cells, the width must be adapted to a distance between the individual lattices, that is to say the (peripheral) width of a cell. A person skilled in the art will do this automatically on the basis of his knowledge in the art. In this case the at least one region of the implant is preferably a "crown" at an end of the implant.

Irregular stresses on the implant can be prevented advantageously if a plurality and/or a multiplicity of separating structures are provided, which divide the receptacle into a corresponding number of receptacle sectors. A particularly homogeneous stressing of the implant when clamped in the release device can be achieved if the multiplicity of separating structures are distributed uniformly along the edge of the clamping body and/or uniformly in the peripheral direction. In general, a non-uniform distribution would also be possible however.

The implant can be axially fixed in the release device in a particularly effective manner if the clamping body has at least engagement element, through which the at least one extension engages in the held state so as to provide the positive fit with the at least one region of the implant. In this context an engagement element is to be understood to mean any element considered expedient by a person skilled in the art, in, which the extension can engage and/or through which the extension can engage, either directly or indirectly. It would accordingly also be conceivable to provide a median structure in the space between the extension and the region of the implant involved in the positive fit, for example a resilient membrane that for example assists or smooths the interaction of the connecting parts for protection thereof. The engagement element is preferably a through-element, such as an opening and/or recess, whereby this can be formed easily in the clamping body. A number of engagement elements and the position thereof is advantageously adapted to a number of extensions and/or webs and the position thereof.

In accordance with an advantageous embodiment, the clamping body has at least one insertion aid, which is designed to guide the insertion of the at least one region of the implant. The at least one region of the implant can thus be supplied in a particularly reliable and intuitive manner sensitive to manipulation. The insertion aid may be formed by any element considered suitable by a person skilled in the art, such as a recess, a rail, a channel, a sliding surface, etc. The insertion aid may be formed as a sliding surface, against which the at least one region of the implant rests as it is supplied to the clamping body or received, at least in part. This can be easily implemented from a design point of view if the insertion aid is arranged before the receptacle of the clamping body in a direction of supply when introducing the at least one region of the implant into the clamping body.

A compact and easy-to-operate clamping body can be provided if the insertion aid is formed as an outer surface and/or lateral surface of part of the clamping body and/or cylinder portion, which runs coaxially with at least one of the insertion elements. The supply process can be carried out in a particularly simple manner in this instance if the at least one receptacle or the at least one slit is arranged and/or shaped in a part of the clamping body and/or cylinder portion that axially directly adjoins the part with the insertion aid. In this case, the part with the at least one receptacle is preferably thicker in the radial direction than the part with the insertion aid. A particularly uniform supply can be achieved if the insertion aid is additionally formed as a centering aid.

The clamping body preferably has two, a plurality of and/or a multiplicity of webs, whereby the implant can be held securely. These are advantageously distributed symmetrically and/or uniformly over a peripheral edge of the clamping body. The implant can thus be held particularly homogeneously and uniformly by the clamping body. In principle, a non-uniform distribution would also be conceivable. The webs are advantageously arranged on the end of the clamping body arranged opposite an end to which the implant can be supplied. In an advantageous embodiment, the clamping body has an even number of webs. In this case, two webs in each case are radially opposed based on the inner axis and/or in the assembled state based on the inner insertion element. In the clamped state, the region of the implant can be arranged such that the webs of the clamping body surround the clamping body in the direction of extension or in the peripheral direction.

The clamping body is advantageously fastened to one of the insertion elements and in particular to the inner insertion element. The clamping body and therefore the implant can thus be moved in a particularly captive manner with the insertion element during implantation. In an alternative or additional embodiment, the clamping body can be fastened to another element of the insertion device, and in particular to a stopper arranged on the inner insertion element.

Any type of connection considered expedient by a person skilled in the art, such as a non-positive fit, a positive fit or an integral bond, for example by means of welding, soldering, screwing, nailing, or gluing, can be considered for both fastening variants. A fastening that is to be obtained with simple design can be achieved if the clamping body is glued onto the inner insertion element and/or to the stopper. This is advantageously achieved by means of a UV-curable adhesive, whereby an easily controllable and manageable procedure can be applied.

It is further proposed for the clamping body, and in particular a contact surface of the at least one receptacle or the at least one slit, to have a material of high static friction so as to hold the implant in position in the clamped state, whereby the implant can be fixed in a manner of simple design. In this case, the static friction is generated between the clamping body and the at least one region of the implant in the insertion device. The material can be any material considered expedient by a person skilled in the art, such as a polymer in particular, and in particular a material selected from the group consisting of polyamide, polyester, polyether block amide, silicone and polyurethane. The clamping body can hereby be designed in particular with low weight. Particularly reliable positioning of the implant in the insertion device can advantageously be achieved due to its high static friction, for example if the material is a polyether block amide, such as PEBAX, from Arkema. All degrees of hardness can be used in this case.

A versatile clamping body that can be used for many applications can advantageously be provided if it has a material that is selected from the group consisting of spring steel, acrylonitrile butadiene styrene (ABS), polycarbonate or polyamide. The material is advantageously a plastics material, such as polyamide (PA) or acrylonitrile butadiene styrene (ABS). Such a material enables easy production of the clamping body, since it can be easily molded. They are therefore ideal for thin-walled components. These materials are also biocompatible. Since these materials are breakproof, a clamping body can also be produced from one of these materials in a particularly resistant manner. For example, if the material is a metal, such as (spring) steel, nitinol, tantalum, gold or platinum, a material that is resistant in particular against bodily fluids for example can be used. In addition, the clamping body could have a further function with use of a metal that is a radiopaque metal, such as tantalum, gold or platinum, thus saving space and facilitating assembly.

In a preferred embodiment the clamping body is formed by a monolayer design. Alternatively, a multilayer design would also be conceivable. To increase the clamping force or holding force, a clamping surface region may have a coating used to increase the friction between these components. To this end, the coating preferably has a material of high static friction (see above for possible materials) so as to hold the implant in position in the clamped state, whereby the implant can be fixed in a manner of simple design. A further layer or a connection layer can be provided for effective contacting of the respective area and of the coating, the layer preferably being made of a material that is suitable as an adhesion promoter, such as a linear low density polyethylene (LLDP).

In a further embodiment of the invention, it is proposed for the clamping body to have a passage for one of the insertion elements. This allows a compact arrangement, which stabilizes and protects the insertion element passed through. If the insertion device is a catheter, the insertion element in question may be an inner shaft of the catheter.

In the embodiment with one of the clamping surface regions on at least one of the extensions, wherein the at least two clamping surface regions clamp therebetween at least the one region of the implant in the clamped state, the at least one extension abuts an outer face of the implant in the clamped state, at least via the at least one clamping surface region. The connection between the clamping body and the implant can thus be released particularly gently. The at least one extension therefore advantageously interacts without engagement with the region of the implant. Furthermore, the at least one clamping surface region contacts the outer face of the region of the implant in the clamped state. It is advantageously possible to dispense with additional connection means, as are known from the prior art (for example hooks and eyelets). The outer face of the region of the implant preferably extends substantially parallel to an inner axis of the implant, wherein this inner axis runs substantially parallel to the inner axis of the clamping body. In addition, the outer face points substantially radially away from the inner axis of the implant. In an advantageous embodiment, at least the two clamping surface regions abut the outer face of the region of the implant in the clamped state. For abutment of the clamping surface regions without engagement, the dimensions of the clamping surface regions, such as length and/or width, have to be adapted to conditions of the outer face of the implant, such as the presence of recesses and/or protrusions, etc. For example, if the implant is a stent having rhombic recesses, either the length or width or both of the clamping surface regions has to be larger than the corresponding dimensions of the recess. A person skilled in the art would implement this automatically on the basis of his common general knowledge in the art.

In an alternative embodiment it is proposed for the clamping body to have at least one ring segment. The at least one ring segment preferably runs in an undulating manner in the radial direction, whereby a spring property of a ring having an undulating ring segment can be implemented with simple design. The phrase "the at least one ring segment runs in an undulating manner in the radial direction" is to be understood to mean that the ring segment has a depression or a minimum that points toward the inner axis of the clamping body in the radial direction and is flanked by two protrusions or maxima. In this case, a clamping surface region may advantageously be arranged on a radially inner end of the depression. A good clamping effect can be achieved if the clamping body has at least two ring segments arranged substantially radially opposed. With regard to the definition for "substantially radially opposed", reference is in turn made to the definition in the text above. The clamping body preferably includes a ring, which has a peripheral undulation in the peripheral direction.

In accordance with a further aspect of the invention, an insertion device for insertion of a medical implant is proposed, the implant being releasable by a relative movement between a first and a second insertion element, the insertion device including a release device for releasing the medical implant, the release device having an indirect and/or direct clamping body for clamping the implant in the insertion device, with a proximal end, which is remote from a distal end of the insertion device during use, and with a distal end, which faces the distal end of the insertion device during use, wherein the clamping body and at least one web has at least one extension and at least two clamping surface regions, wherein the extension can be arranged so as to be oriented substantially in the radial direction relative to an inner axis of the clamping body, and wherein the at least two clamping surface regions are arranged so as to be substantially pointing toward one another and are aligned substantially parallel to one another, wherein the at least one web or the at least one extension includes at least one of the two clamping surface regions, and wherein the at least two clamping surface regions and/or the at least one extension non-positively and/or positively connect/connects the at least one extension to at least one region of the implant in the clamped state.

As a result of the embodiment according to the invention, an insertion device can be provided, the implant being held securely therein or being fastened securely on the inner shaft of the insertion device. The clamping body also allows a compact and simple design of the insertion device. An undesired movement of the implant, for example jumping, when the implant is fed to the site of implantation and/or when the implant is released can also be prevented. The release device is thus of compact and simple design. In addition, the implant can be assembled easily on the insertion device or on the catheter, for example in the preparation lab. Release of the implant is advantageously reliable and quick. In addition, jamming of the respective release device can be eliminated by the minimized risk of deformation of the implant. The partially released implant can particularly advantageously be repositioned by means of the embodiment according to the invention. In addition, a function test of the implant can be carried out and, in the case of defect, the faulty implant can be removed. The insertion device may advantageously be a catheter. The insertion device can be used particularly advantageously for assembly and release of a prosthesis, a cardiac valve or a stent.

For example, the insertion device can be formed in two variants. These variants differ with regard to the end at which release of the implant begins. This can occur either at the distal end, which is arranged in the direction of the distal end of the insertion device, or at the proximal end, which is arranged in the direction of the proximal end of the insertion device. Each insertion device is moved in a direction of insertion. In this context, "the direction of insertion" is to be understood to mean the direction along which the insertion device is introduced together with the release device and the implant into the human and/or animal body. In particular, it points from the proximal end to the distal end of the insertion device.

If the release of the implant begins at the distal end thereof, the release device can be used for a "distal" insertion device. In this case the inner insertion element (first insertion element) is connected to the tip of the insertion device, such as the tip of a catheter. By contrast, the outer insertion element (second insertion element), which is arranged radially around the inner insertion element, is not connected to the tip of the catheter and can be moved relative to the tip of the catheter by an axial movement in the direction of the proximal end of the insertion device. An implant arranged radially between the inner and outer insertion element can thus first be exposed via its distal end for implantation or expansion.

If the release device is designed in accordance with the alternative embodiment, in which the release of the implant begins at the proximal end thereof, the release device can be used for a "proximal" insertion device. In this case the outer insertion element is connected to a tip of the insertion device, and by contrast the inner insertion element is not. The outer insertion element is coupled to a guide element for movement. The guide element runs coaxially with the inner insertion element and therein and is formed for example by a shaft having an insertion wire and a lumen. The guide element is connected to the proximal end of the insertion device for manipulation by an operator. The guide element is also connected to the tip. If the insertion element is then displaced in the direction of the distal end of the insertion device, it pushes both the tip and the outer insertion element into the distal direction, whereby an opening and/or a gap is produced and an implant arranged radially between the inner and outer insertion element can first be exposed via its proximal end for implantation or expansion.

In accordance with the alternative embodiment with the release first of the proximal end of the implant, the insertion device can particularly advantageously be used when implanting asymmetrical implants, such as in cardiac catheter applications.

In addition, it is proposed for the insertion device to have a stopper, which limits a movement of the implant in the direction of a proximal end of the insertion device. This is achieved with an insertion device in which the release of the implant begins at the distal end of the implant. By contrast, with an insertion device in which the release of the implant begins at the proximal end thereof, the stopper limits a movement of the implant in the direction of a distal end of the insertion device. Such movements may disadvantageously lead to jamming of the implant. A preferred development consists in the clamping body abutting the stopper, thus clearly defining a position of the clamping body during the movement of the outer insertion element in the direction of a proximal or distal end of the insertion device or during the relative movement of the two insertion elements. For example, if this stopper is arranged at the proximal end of the clamping body, this can additionally provide a contact area for a sliding movement of the implant in the insertion device.

The stopper may further be connected to the clamping body, whereby the clamping body is effectively prevented from shifting relative to the stopper. In this case, any type of fastening considered expedient by a person skilled in the art, such as a non-positive fit, a positive fit or an integral bond, can be considered. The stopper may be a component of one of the parts and/or the cylinder portions of the clamping body and/or of the at least one receptacle and/or of the fastening element and/or a base of the bushing and/or creates the fastening to one of the insertion elements or to the inner insertion element. The clamping body is particularly preferably formed integrally with the stopper, whereby the arrangement can be formed in a very stable manner. In this case, "integrally" is to be understood to mean that the stopper and the clamping body are formed by the same component and/or can only be separated from one another with a loss of function of at least one of the components. The stopper may advantageously be the at least one separating structure of the at least one receptacle. The stopper can be made of any of the above-mentioned materials. The stopper preferably has a polymer as its material, and in particular a polymer selected from the group consisting of polyester, polyether block amide, silicone, polyurethane and polyamide.

In accordance with an advantageous embodiment, the implant may be a self-expanding implant, whereby it can open automatically in the absence of the outer insertion element and/or upon exit from the clamping body. In this case, the implant can open the at least one web of the clamping body by means of its radial force. Due to the self-expanding implant, an additional expanding means can be omitted. Space and assembly effort for this can therefore be saved. The insertion device can thus also be formed in a less complex manner. In principle however, it would also be possible to use a balloon-expandable implant. To this end, the insertion device would have to be adapted accordingly however, which a person skilled in the art achieves independently on the basis of his common general knowledge in the art. The implant is particularly advantageously formed without fastening elements, in other words without hooks, eyelets or the like, whereby the implant can be shortened compared to implants of the prior art. This has a positive effect above all for the patient. The insertion device consequently can also be formed without fastening elements. When the implant is assembled, the insertion device thus foregoes an otherwise fragile connection of fastening elements, such as hooks and eyelets, whereby rejection due to incorrect assembly is reduced, thus saving costs. This results above all in a time saving when preparing the insertion device in the preparation lab.

In addition, a method for holding a medical implant by means of a clamping body of a release device in an insertion device, in which the implant is released by a relative movement between a first and a second insertion element, is proposed The clamping body includes a proximal end, which is remote from a distal end of the insertion device during use, and includes a distal end, which faces the distal end of the insertion device during use. The method has at least the following steps: Insertion of at least one region of the implant into the clamping body so that the at least one region is arranged radially between at least two clamping surface regions, wherein at least one of the two clamping surface regions is arranged either on at least one web or on a lateral surface of a receptacle of the clamping body or on at least extension of the clamping body that can be arranged substantially in the radial direction relative to an inner axis of the clamping body; placing the clamping body together with the implant in at least one insertion element and thus either producing a positive fit between the at least one extension and the at least one region of the implant, wherein at least one of the two clamping surface regions is arranged on the at least one web or on the lateral surface of the receptacle of the clamping body, or clamping the at least one region radially between the at least two clamping surface regions, wherein at least one of the two clamping surface regions is arranged on the at least one extension of the clamping body.

As a result of the embodiment according to the invention, a method can be provided, by means of which an implant can be placed and fastened precisely and quickly in the insertion device in a user-friendly manner. With an implant thus connected to the release device, an undesired movement of the implant, for example jumping, when the implant is fed to the site of implantation and/or when the implant is released can be prevented. In addition, the handling and assembly of the implant in the insertion device, for example a catheter, is highly simplified in the preparation lab. Furthermore, the implant can be released reliably and quickly. The already partially released implant connected to the release device by means of the method according to the invention can particularly advantageously be repositioned in a user-friendly manner. In addition, a function test can be carried out on an implant thus fastened and, in the case of defect, the implant can be removed.

DESCRIPTION OF THE DRAWINGS

The invention will be explained in greater detail hereinafter by way of example with reference to exemplary embodiments illustrated in drawings, in which:

FIG. 5 shows a schematic illustration of the insertion device and the clamping body from FIG. 1 with the implant placed in position before an outer insertion element is slid on;

FIG. 7 shows a schematic illustration of the insertion device and the clamping body from FIG. 1 with the implant placed fully in position once the outer insertion element has been slid on;

FIG. 9 shows a schematic illustration of an alternative proximal insertion device and the clamping body from FIG. 1 with the implant placed fully in position once an outer insertion element has been slid on;

FIG. 14 shows a schematic illustration of the insertion device and the clamping body from FIG. 11 with the implant placed in position before an outer insertion element is slid on;

FIG. 15 shows a schematic illustration of the insertion device and the clamping body from FIG. 11 with the implant placed fully in position once the outer insertion element has been slid on;

FIG. 22 shows a schematic illustration of an alternative proximal insertion device and of the clamping body from FIG. 12 with the implant placed fully in position once an outer insertion element has been slid on.

DETAILED DESCRIPTION

In the figures, functionally like or similarly acting elements are denoted in each case by like reference signs. The figures are schematic illustrations of the invention. They do not show specific parameters of the invention. The figures also merely reproduce typical embodiments of the invention and are not intended to limit the invention to the embodiments illustrated.

Figure 1:
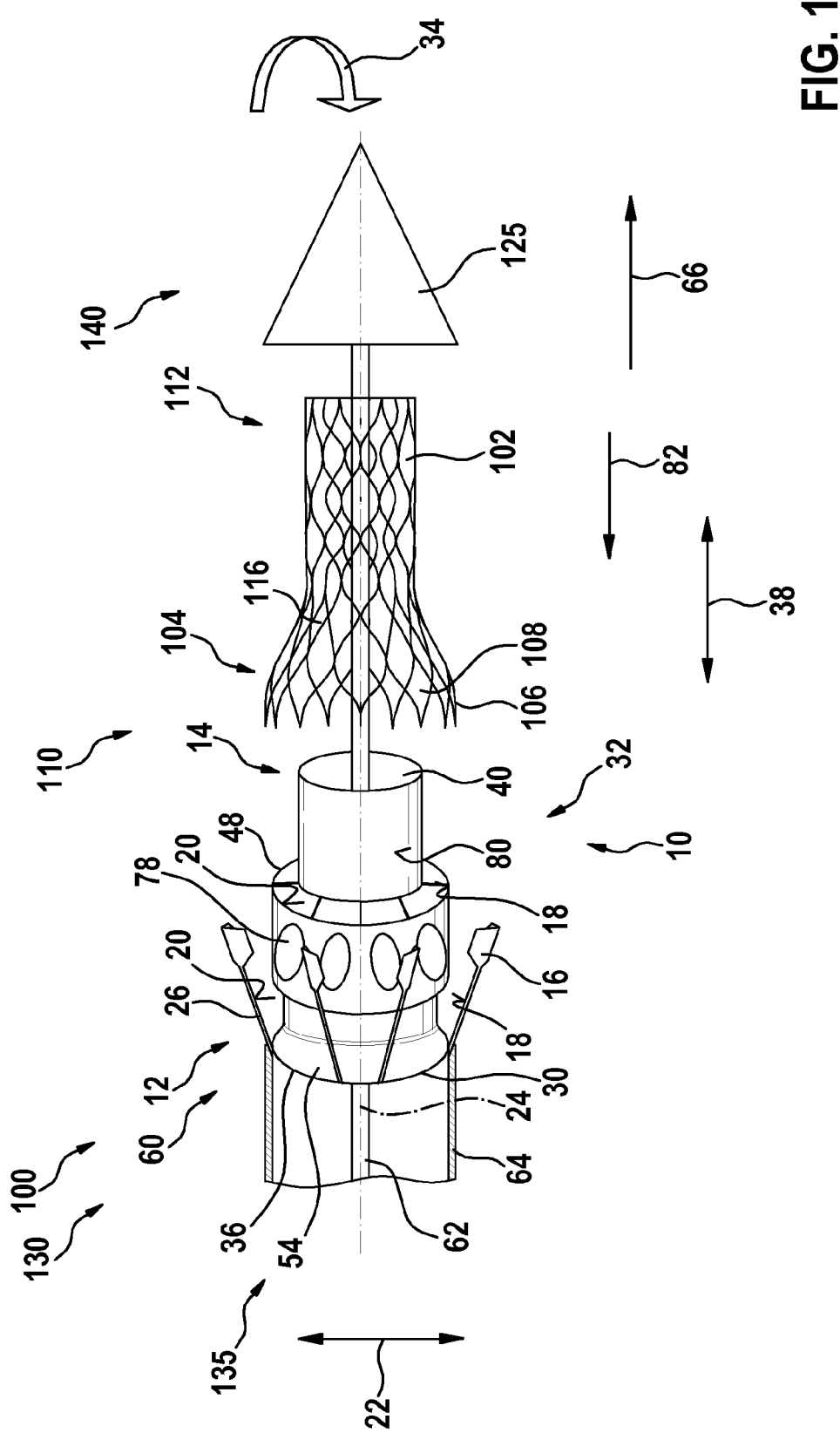
FIG. 1 shows a schematic illustration of a section through a preferred and advantageous exemplary embodiment of a distal insertion device and of a release device according to the invention with a clamping body and an implant.
Figure 7:
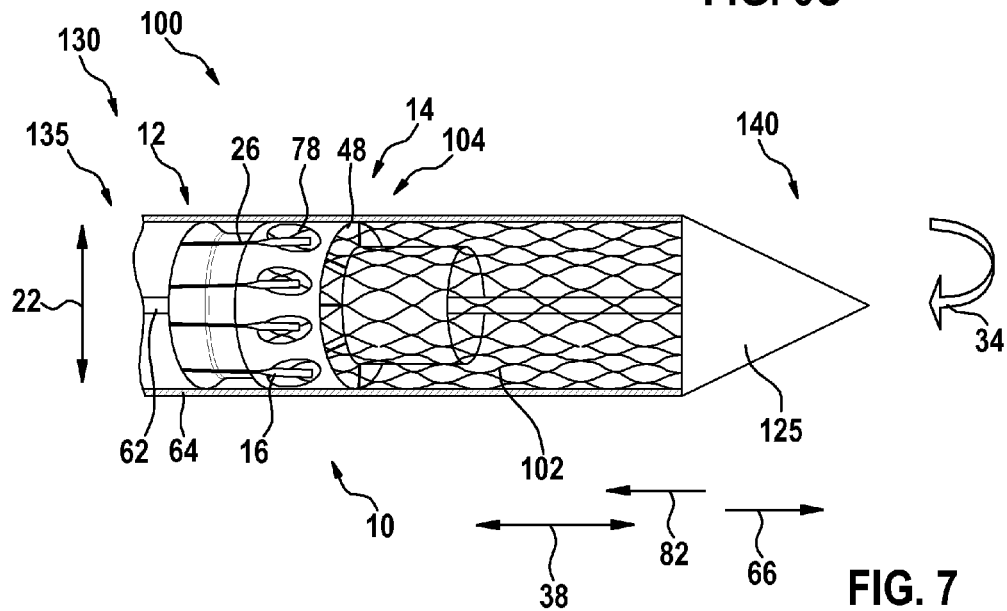

FIG. 1 shows a longitudinal section through a preferred exemplary embodiment of a release device 100 of a distal insertion device 130, which is only illustrated in part. For example, the insertion device 130 is a catheter having a shaft region 60 with two coaxially arranged insertion elements 62, 64, for example an inner shaft (insertion element 62) and an outer shaft (insertion element 64), which surrounds the inner shaft and in turn can be surrounded by an outer sleeve (not shown). The proximal end 135 of the insertion device 130 faces a user during use, that is to say as the implant 102 is fastened to the release device 100 or during implantation. The implant 102 is placed at the distal end 140 of the shaft region 60 between the inner shaft and the outer shaft and is to be released at the site of implantation in the animal or human body (see FIG. 7).

The release device 100 is used to release the medical implant 102 from the insertion device 130. The implant 102 is arranged at an end 140 of the shaft region 60 remote from the user, for example in the vicinity of the tip of a catheter 125. For example, the implant 102 is placed around the inner insertion element 62 and is released by a relative movement between the first and the second insertion element 62, 64 beginning at a distal end 112 of the implant 102. In this case, the inner insertion element 62 is connected to the tip of the catheter 125, but by contrast the outer insertion element 64 is not.

Figure 2:
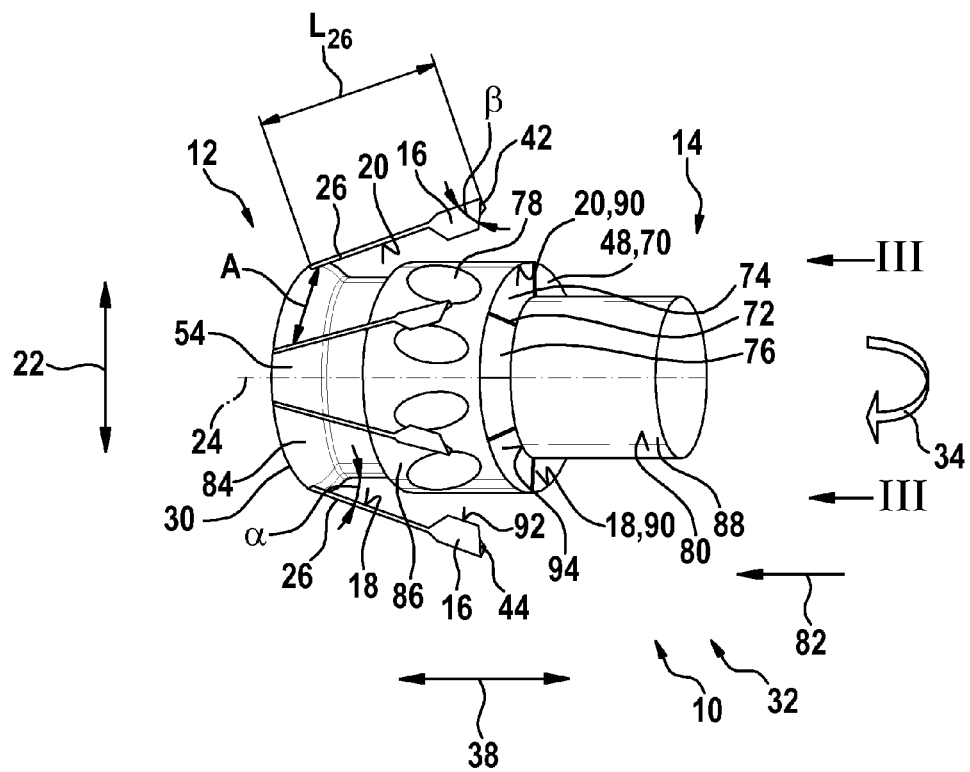
FIG. 2 shows an enlarged schematic illustration of the clamping body of FIG. 1.

The release device 100 includes a clamping body 10 for clamping the implant 102 in the insertion device 130. As in FIG. 2, which shows an enlarged view of the clamping body 10, the clamping body 10 has a proximal end 12, which is remote from the distal end 140 of the insertion device 130 during use, and a distal end 14, which faces the distal end 140 of the insertion device 130 during use. The clamping body 10 is formed by a cylindrical and/or bushing-shaped element. A cylinder jacket 32 of the clamping body 10 extends in the peripheral direction 34 around an inner axis 24 of the clamping body 10 and, when assembled in the insertion device 130, around the inner insertion element 62. The cylinder jacket 32 has three cylinder portions 84, 86, 88 in the axial direction 38, which differ in terms of their radial width. The two outer cylinder portions 84, 88, or the two cylinder portions 84, 88 arranged at the proximal and distal ends 12, 14 of the clamping body, have substantially the same radial extension. By contrast, the middle cylinder portion 86 arranged therebetween has a greater radial extension than the cylinder portions 84, 88.

At its proximal end 12, the clamping body 10 has a base 36, which extends substantially perpendicular to the inner axis 24 of the clamping body 10 or, in the assembled state, substantially perpendicular to the inner insertion element 62. The webs 26 protrude from this base 36 substantially in an axial direction 38 along the inner axis 24 of the clamping body 10. The clamping body 10 is fastened or glued to the inner insertion element 62 via this base 36. To this end, the clamping body 10 or the base 36 has a passage 40 for the inner insertion element 62. The fastening is achieved for example by means of a UV-curable adhesive.

To limit a movement of the implant 102 in the direction of the proximal end 135 of the insertion device 130, the insertion device 130 has a stopper 145. This stopper 145 is formed by separating structures 72 of a receptacle 48 of the clamping body 10 (see below) and is thus designed integrally with the clamping body 10.

The clamping body further has a multiplicity of webs 26, which protrude from the proximal end 12 of the clamping body 10 substantially in an axial direction 38 along the inner axis 24 of the clamping body 10. The webs 26 are also distributed symmetrically or with uniform spacing A over an edge 30 or a periphery of the clamping body 10. In addition, the webs 26 are arranged relative to the inner axis 24 and to the inner insertion element 62 at an angle α of substantially 30° in an axial neutral position of the clamping body 10 shown here, that is to say in the state without axial fixing of the implant (see FIG. 2).

Alternatively, the clamping body 10 may have at least two radially opposed bridges instead of the base 36, the bridges being arranged substantially perpendicular to the inner axis of the clamping body and being fastened via their radially inner ends on the inner insertion element 62. In this case, the radially outer ends of the bridges would contact the cylinder jacket 32. This could be a ring, from which the webs 26 protrude substantially in the axial direction 38 (not shown). In principle, for stable and homogeneous fastening, it would also be conceivable the design the cylinder portions 84, 86, 88 so as to be solid, apart from the passage 40 for the inner insertion element 62 and the receptacle 48 for the region 104 of the implant 102 (for details see below).

Figure 3:
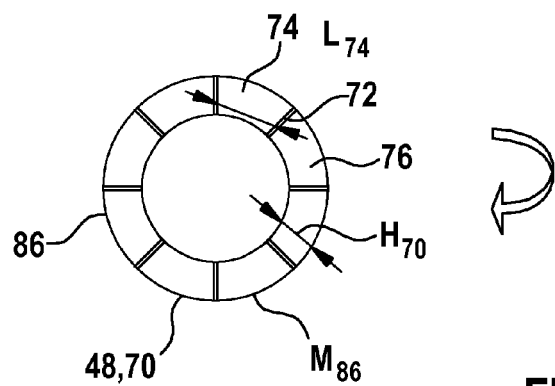
FIG. 3 shows a schematic illustration of a detail of a receptacle of the clamping body from FIG. 1.

The middle cylinder portion 86 includes the receptacle 48 for the region 104 of the implant 102. This receptacle 48 is designed as a slit 70, which extends completely along an edge 30 of the clamping body 10 in the peripheral direction 34. Its radial height $H_{70}$ corresponds approximately to a difference between the extensions of the cylinder portions 84, 88 and 86 minus a material thickness $M_{86}$ of a delimitation of the receptacle 48 of the cylinder portion 86 (see also FIG. 6B). As is indicated in FIG. 3, which shows a view in the direction of the arrows in FIG. 2, the height $H_{70}$ of the slit 70 is matched to a material thickness of the region 104 of the implant 102.

The receptacle 48 or the slit 70 is divided by means of a plurality of separating structures 72 in the form of radially running webs into a corresponding number of receptacle sectors 74, 76 (merely two receptacle sectors are denoted by reference numerals). The separating structures 72 are distributed in a uniformly spaced manner. An outer lateral surface of the cylinder portion 88 at the distal end 14 of the clamping body 10 is used as an insertion aid 80 so as to facilitate and to guide a supply of the region 104 of the implant to the receptacle 48. The insertion aid 80 is accordingly arranged before the receptacle 48 of the clamping body 10 in a supply direction 82 when inserting the region 104 of the implant 102 into the clamping body 10. Due to the coaxial arrangement of the cylinder portion 88 with the inner insertion element 62, this can additionally be used as a centering aid.

Figure 4:
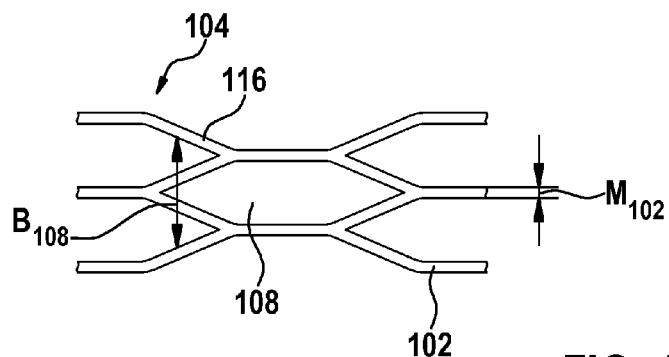
FIG. 4 shows a schematic illustration of a detail of a region of the implant from FIG. 1.

As a result of the insertion of the region 104 of the implant 102 into the receptacle 48, this is held on the basis of a radially outer lateral surface 90, which has at least two clamping surface regions 18, 20, which point toward one another and are aligned parallel to one another, since the two clamping surface regions 18, 20 clamp therebetween the region 104 of the implant 102. In addition, the region 14 and therefore the implant 102 is fixed in a manner secured against rotation with the aid of the separating structures 72 in the receptacle 48 in the peripheral direction (see FIG. 5). The region 104 of the implant 102 is formed by a crown-shaped cell or rhombic recess 108. A length $L_{74}$ of a receptacle sector 74 in the peripheral direction 34 is in this case matched to a width $B_{108}$ of the recess 108 and, for example, is the width $B_{108}$ of the recess 108+0.1 mm and/or is approximately 1 mm to 2.5 mm (see FIG. 4).

To hold the implant 102 in a held position of the clamping body 10, the clamping body is formed as a hasp. To this end, the clamping body 10 has an extension 16 at each distal end 42 of the webs 26. The extension 16 is arranged at an angle β of substantially 70° on a web 26. Each extension 16 is thus arranged so as to be oriented substantially in the radial direction 22 relative to the inner axis 24 of the clamping body 10 (see FIG. 2). The webs 26 and the extensions 16 are formed integrally with one another or as a component, wherein the webs 26 can be interconnected via a ring 54 fastened to the cylinder portion 84. A radially inner end 44 of each extension 16 is planar or flat and forms a contact surface 92 for abutting a radially inner lateral surface 94 of the receptacle 48 (see FIG. 6C).

Figure 5:
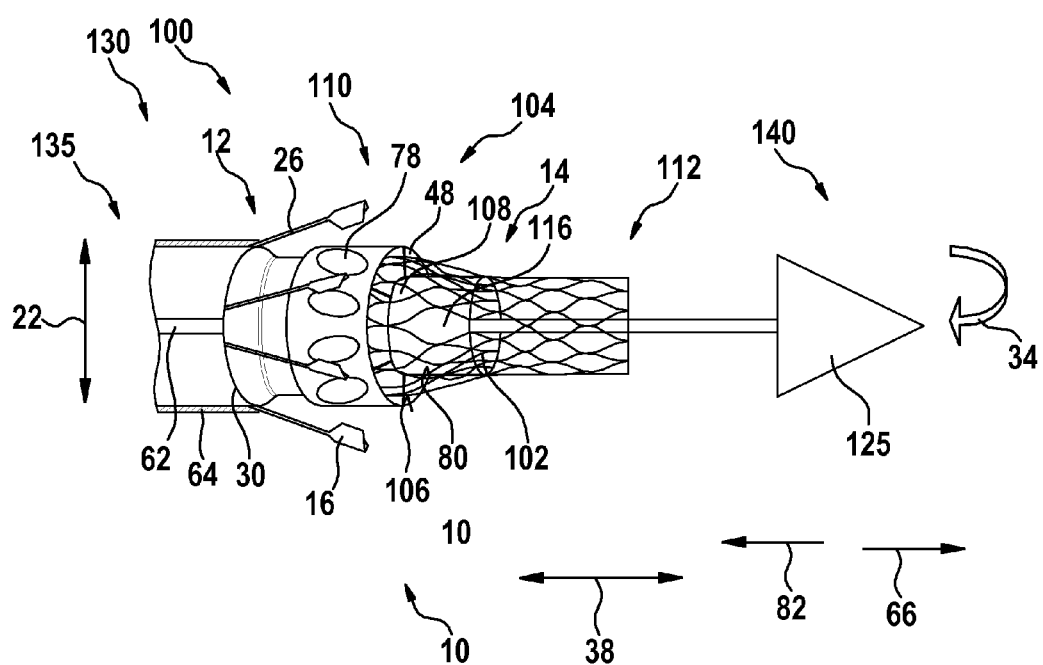

FIG. 5 shows the region 104 of the implant 102 in its clamped state in the clamping body 10 or the receptacle 48 thereof. In this case, the clamping body 10 can be understood to be a direct clamping body 10 for the implant 102. To establish the held state, in particular for axial holding of the implant 102, the clamping body 10 has to be transferred from its neutral position into its held position. To this end, the webs 26 are formed resiliently, whereby they, or their distal ends 42 with the extensions 16, can be moved radially relative to the inner axis 24. This can be achieved by a suitable material of the webs 26. In principle, it would also be conceivable to form a contact region between the base and the web in an articulated manner or with a hinged joint. The webs 26 are moved by sliding the outer insertion element 64 over the clamping body 10 in the direction of the distal end 140 of the insertion device 130. In this case, clamping surface regions 18, 20 on the webs 26 come into contact with an outer lateral surface of the cylinder portion 86 and additionally clamp the clamping body 10. The implant 102 is thus also clamped in the release device 100, whereby the outer insertion element 64 can be understood to be an indirect clamping body 10 (see FIG. 7).

Figure 6A:
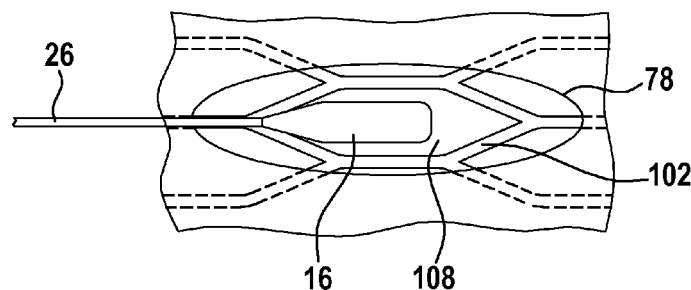
FIG. 6A shows a schematic illustration from above of an extension of the clamping body from FIG. 1 with engagement by an engagement element and into the implant from FIG. 4.

So that the extensions 16 can hold the region 104 of the implant 102, the clamping body 10, in the middle cylinder portion 86 in which the receptacle 48 is also arranged and in which the region 104 is radially clamped, includes a plurality of engagement elements 78, or a number of engagement elements corresponding to the number of extensions 16. If the outer insertion element 64 is then slid over, the extensions 16 are then moved so far radially relative to the inner axis 24 that each extension 16 engages in an engagement element 78 or engages therethrough. The engagement elements 78 are distributed in the peripheral direction 34 such that they are each placed substantially centrally in the peripheral direction 34 on a receptacle sector 74, 76. If an extension 16 then engages through an engagement element 78, it also engages into the cell 92 of the implant 102 placed in the receptacle sector 74, 76, and the extension 16 positively connects in the clamped state to the region 104 of the implant 102, whereby the implant 102 is fixed axially in the clamping body 10 (see FIG. 6A).

The dimensions of the clamping body 10, of the receptacle 48 and of the extensions 16 are matched to one another and to the dimensions of the outer insertion element 64. An inner diameter $D_{126}$, which is adjustable in the held state, of the webs 26 or of the radial spacing between contact surfaces 92 of opposite extensions 16 is adapted to a contour or an outer diameter $D_{a10}$ of the clamping body 10 or its cylinder portions 84, 86. Furthermore, these parameters of the clamping body 10 are matched to measurements of the insertion device 130, such as an inner diameter $D_{164}$ of the insertion element 64 or of the outer shaft. In this case, an outer diameter $D_{a10}$ of the clamping body 10 may equal the inner diameter $D_{164}$ of the outer shaft minus 0.2 mm (see FIG. 9).

Figure 6B:
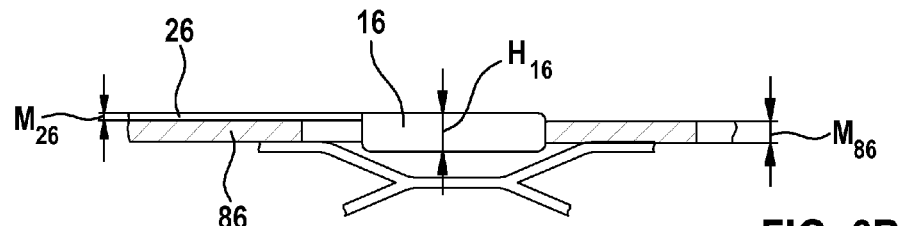
FIG. 6B shows a schematic illustration from the side of the extension from FIG. 6A.
Figure 6C:
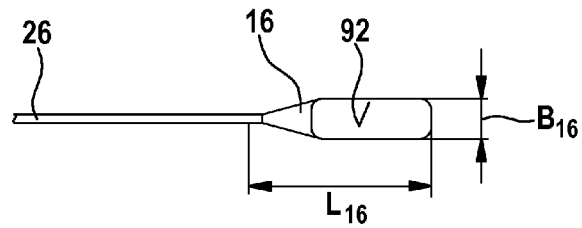
FIG. 6C shows a schematic illustration from below of the extension from FIG. 6A.

A web 26 having an extension 16 is shown in detail from the side and from below in FIGS. 6B and 6C. A length $L_{26}$ of a web 26 is 5 mm to 15 mm for example, wherein the ring 54 may have a length of approximately 5 mm (see FIG. 1). A material thickness $M_{26}$ of the web 26 is 0.1 mm to 0.2 mm for example. Transition regions from the web 26 to the extension 16 may be designed with rounded portions to protect an inner surface of the insertion element 64. A height $H_{16}$ of the extension 16 has to be greater than a material thickness $M_{102}$ of the implant 102 and, for example, is the material thickness $M_{102}$ of the implant 102+the material thickness $M_{86}$ of the delimitation of the receptacle 48 in the cylinder portion 86+0.2 mm or is approximately 1 mm to 2 mm. For the positive fit, a width $B_{16}$ of the extension 16 has to be at least smaller than the rhombic recess 108 of the implant 102 and, for example, is 1 mm to 2 mm. For engagement into the recess 108, a length $L_{16}$ of the extension 16 also has to be smaller than the recess and, for example, is 3 mm to 4 mm. In addition, the radial height $H_{70}$ of the slit 70 must be greater than or equal to the height $H_{16}$ of the extension 16 and, for example, is the material thickness $M_{102}$ of the implant+the material thickness $M_{86}$ of the delimitation of the receptacle 48 in the cylinder portion 86+0.1 mm or is approximately 1 mm to 2 mm. The clamping body 10 and/or the webs 26 and/or the extensions 16 is/are for example made of a hard monolayer design polymer (for example polyamide TR55LX from EMS Chemie) with high friction so as to hold the implant 102 in position in the clamped state.

In principle, the clamping body can also be formed from a radiopaque metal, such as stainless steel, tantalum, gold or platinum. A progression of the inner insertion element, and therefore of the implant, as well as a correct position of the implant at a site of implantation could thus be monitored with use of an x-ray device (not shown here) during implantation of the implant by means of the insertion device.

Figure 8:
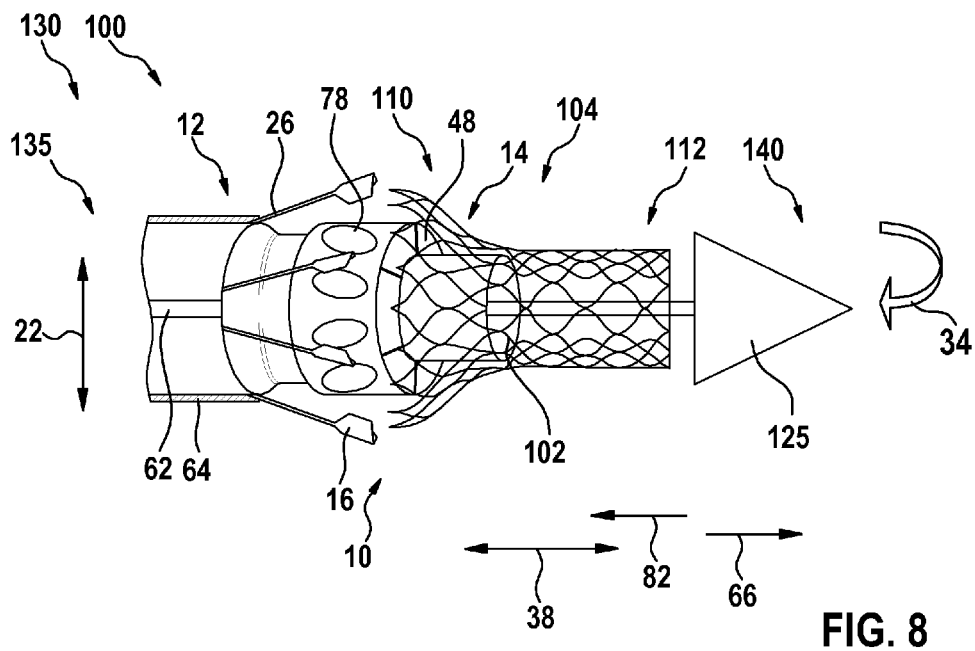
FIG. 8 shows a schematic illustration of the insertion device and the clamping body from FIG. 1 with the implant fully released.

FIG. 1 shows the clamping body 10 arranged in the insertion device 130 before placement of the implant 102. In this case, the outer insertion element 64 is withdrawn in the direction of the proximal end 135 of the insertion device 130 as far as the axial position of the base 36 of the clamping body 10. No clamping force is exerted on the webs 26 and the clamping body 10 is in its axial neutral position. The placement of the implant 102 in the receptacle 48 of the clamping body 10 is shown in FIG. 5. The implant 102, for example a stent or an artificial cardiac valve implant, is self-expanding and is formed with no fastening elements. A method for clamping the implant 102 by means of the clamping body 10 is described hereinafter with reference to FIGS. 5, 7 and 8.

In this case, a proximal end 110 of the implant 102, which is crimped onto the inner shaft, is introduced with the inner shaft with the aid of the insertion aid 80 into the receptacle 48 of the cylinder jacket 32 of the clamping body 10 in a first step. This occurs in the supply direction 82 or from the direction of the distal end 14 of the clamping body 10. The sliding movement takes place for example until a node point 116 on the proximal end 110 of the implant 102 contacts the stopper 145 or the separating structures 72. The stopper 145 thus limits the movement of the implant 102 in the direction of the proximal end 135 of the insertion device 130. The implant 102 is then placed such that the region 104 is arranged radially between the clamping surface regions 18, 20 of the radially outer lateral surface 90 of the receptacle 48 (see FIG. 5).

In a subsequent, second step the clamping body 10 together with the implant 102 is placed in the outer insertion element 64. This occurs by moving the outer insertion element 64 in the direction of the distal end 140 of the insertion device 130. The webs 26 are thus pushed radially inwardly due to their spring property and the extensions 16 engage into the engagement elements 78 and establish the positive fit to axially fix the implant 102. In addition the webs 26, in the clamped state, extend in the axial direction 38 parallel to the inner axis 24 or to the inner insertion element 62 and are arranged around the proximal end 110 of the implant 102 in the peripheral direction 34. The extensions 16 are then arranged substantially perpendicular to the inner axis 24 or to the inner insertion element 62 (see FIG. 7). The clamping body 10 is thus placed with the implant 102 in the outer insertion element 64 and assembly is complete.

In the clamped state, interaction between a holding force of the insertion element 64 and the resilience of the webs 26 holds the clamping body 10 and therefore also the implant 102 in position. In addition, the clamping body 10 has a high static friction due to its material properties. As a result of the static friction between the clamping body 10 and the implant 102, the clamping body 10 has a holding force that additionally holds the implant 102 in position in the insertion device 130 in the clamped state, whereby the implant 102 is prevented from sliding out. The following definition can be given for the static friction $F_H$: $F_H = \mu_H \cdot F_N$ where: $\mu_H$: static friction coefficient (material-dependent coefficient, material of the clamping body 10 and/or of the implant 102) of the clamping surface regions 18, 20 of the receptacle 48 and an outer surface 106 of the implant 102, $F_N$: nominal force, resulting from the radial force of the insertion element 64 (with reaction of the radial force of the implant 102).

For implantation of the implant 102 in the body, the insertion device 130 thus prepared is introduced into the body (not shown) in a direction of insertion 66. Due to the movement of the outer insertion element 64 in the direction of the proximal end 135 of the insertion device 130, the distal end 112 of the implant 102 is released, the implant opening and being positioned due to its ability to self-expand (not shown). At this stage, the implant 102 is still connected securely via its proximal end 110 to the clamping body 10. If necessary, function tests of the implant 102 can then be carried out. If a malfunction is established, the implant 102 can be removed again from the body. Repositioning of an incorrectly positioned implant 102 is also possible. If the outer insertion element 64 is then withdrawn in the direction of the proximal end 135 of the insertion device 130 until it is axially behind the clamping body 10, a normal force on the webs 26 is removed. In this case, the clamping body 10 moves by the resilience of the webs 26 into the axial neutral position to release the region 104 of the implant 102, whereby the positive fit is released. If the clamping body 10 is then likewise drawn in the direction of the proximal end 135, the proximal end 110 of the implant 102 exits from the receptacle 48 and opens automatically due to its radial force (see FIG. 8). The release device 100 or the clamping body 10 is then withdrawn with the inner shaft into the outer shaft, whereby the clamping body 10 is compressed again, and the insertion device 130 is removed from the body. The implant 102 remains fully positioned in the body (not shown).

Figure 9:
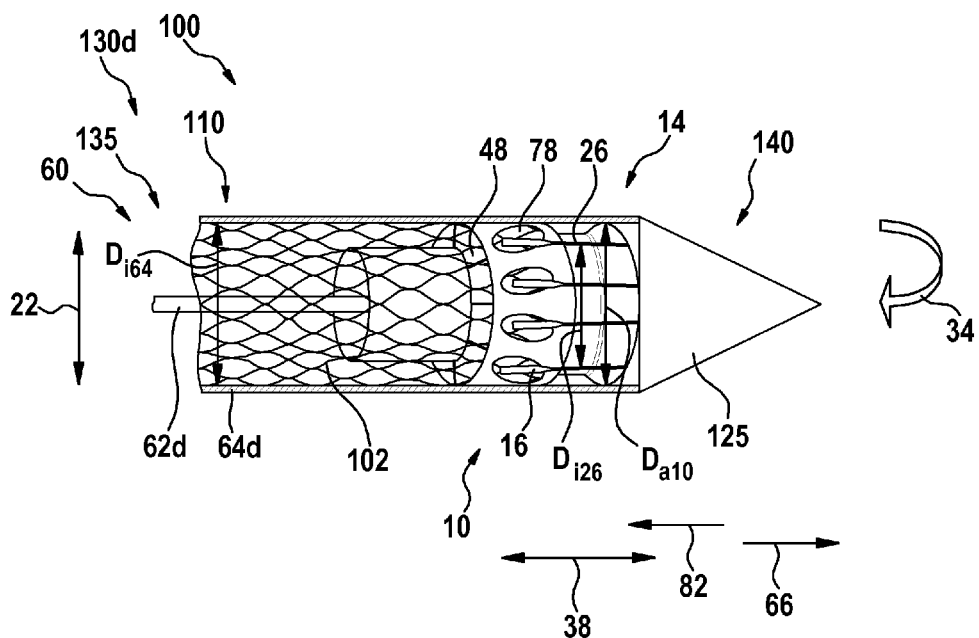
Figure 22:
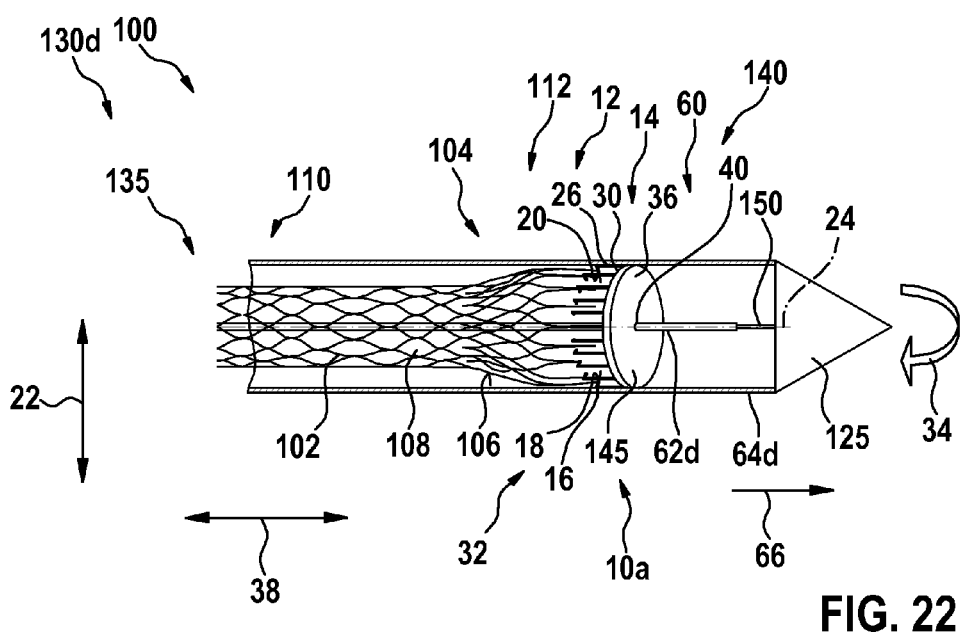
Figure 23:
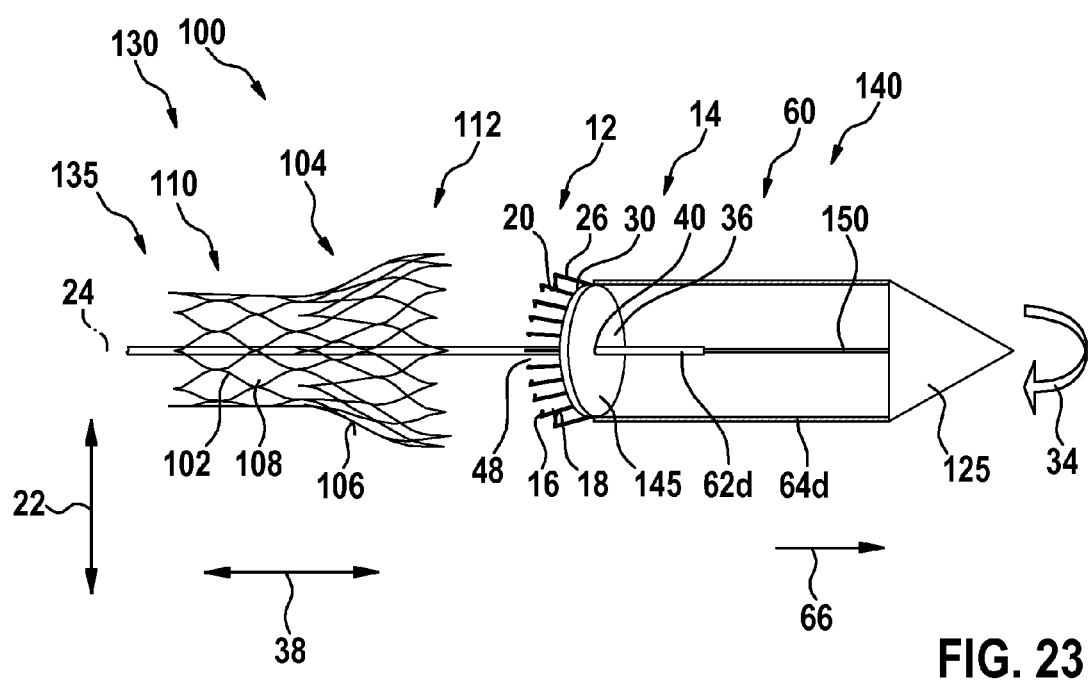
FIG. 23 shows a schematic illustration of the insertion device from FIG. 22 with the implant completely released.

Three alternative exemplary embodiments of the insertion device 130 is illustrated in FIGS. 9 and 23 as well as four alternative exemplary embodiments of the clamping body 10. Like components, features and functions are basically denoted in principle by like reference signs. To distinguish between the exemplary embodiments of FIGS. 9 to 23 and those in FIGS. 1 to 8, however, the letters a to e have been added to the reference signs of differently designed components in the exemplary embodiment of FIGS. 9 to 23. The following description is basically restricted to the differences from the exemplary embodiment in FIGS. 1 to 8, wherein reference can be made to the description of the exemplary embodiment in FIGS. 1 to 8 with regard to like components, features and functions.

FIG. 9 shows a longitudinal section through an exemplary embodiment of a release device 100 of an alternative proximal insertion device 130d. For example, the insertion device 130d is a catheter having a shaft region 60 with two coaxially arranged insertion elements 62d, 64d, for example an inner shaft (insertion element 62d) and an outer shaft (insertion element 64d), which surrounds the inner shaft and in turn can be surrounded by an outer sleeve (not shown). The proximal end 135 of the insertion device 130d faces a user during use, that is to say as the implant 102 is fastened to the release device 100 or during implantation. The implant 102 is placed at the distal end 140 of the shaft region 60 between the inner shaft and the outer shaft and is to be released at the site of implantation in the animal or human body. For example, the implant 102 is placed around the inner insertion element 62d and is released by a relative movement between the first and second insertion element 62d, 64d beginning at a proximal end 110 of the implant 102. In this case the outer insertion element 64d is connected to the tip of the catheter 125, but by contrast the inner insertion element 62d is not. To connect the proximal end 135 of the insertion device 130d and the tip of the catheter 125, the guide device 130*d* has a guide element 150, which runs coaxially with the inner insertion element 62*d* and therein and is formed for example by a shaft having an insertion wire and a lumen (see FIG. 10). The release device 100 includes a clamping body 10, formed similarly to the clamping body 10 of FIGS. 1 to 8, for clamping the implant 102 in the insertion device 130*d*. Compared to the exemplary embodiment in FIGS. 1 to 8 however, the clamping body 10 is in this case arranged on the inner insertion element 62*d*, turned through 180°.

Figure 10:
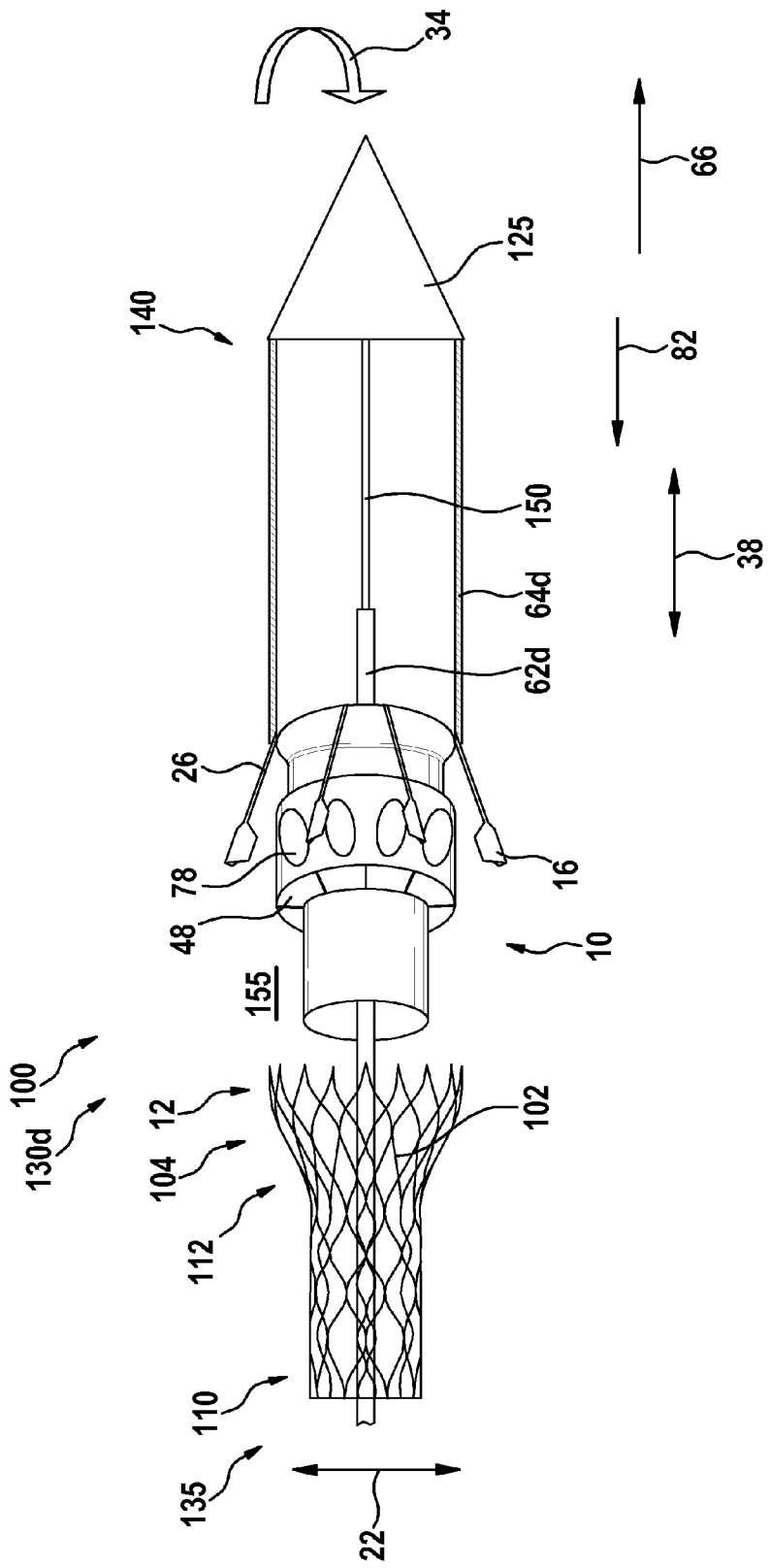
FIG. 10 shows a schematic illustration of the insertion device from FIG. 9 with the implant completely released.

A method for connecting the implant 102 by means of the clamping body 10 and therefore by means of the proximal insertion device 130*d* will now be described with reference to FIGS. 9 and 10. In a first step, the previously cooled, crimped implant 102 is placed on the inner insertion element 62*d*. In this case, the region 104 of the implant 102 is slid over the inner insertion element 62*d* into the receptacle 48 of the clamping body 10. The sliding movement is carried out for example until a node point at the distal end 112 of the implant 102 or of the region 104 contacts the stopper 145 (not shown). The stopper 145 thus limits the movement of the implant 102 in the direction of the distal end 140 of the insertion device 130*d*.

Alternatively, it would also be possible to place the implant 102 on the insertion element 62*d* in the direction of the proximal end 135 of the insertion device 130*d*. In this case, the entire implant 102 is slid over the tip of a catheter 125 and over the inner insertion element 62*d*. In this case, the clamping body 10 would only be applied and fastened to the inner insertion element 62*d* once the implant 102 had been placed in position.

In a second step, the outer insertion element 64*d* is slid on in the direction of the proximal end 135 of the insertion device 130*d*, whereby the clamping body 10 is pressed together or the webs 26 thereof are pressed radially inwardly. The extensions 16 thus enter into insertion elements 78 of the clamping body 10 and into the region 104 to establish a positive fit between the extensions 16 and the region 104 of the implant 102. The clamping body 10 together with the implant 102 is placed in the outer insertion element 64*d* and assembly is complete (see FIG. 9).

For implantation of the implant 102 in the body, the insertion device 130*d* thus prepared is introduced into the body in a direction of insertion 66. Due to the movement of the tip of the catheter 125 and of the outer insertion element 64*d* in the direction of the distal end 140 of the insertion device 130*d* by means of the guide element 150, an opening 155 is released at the outer insertion element 64*d*, the opening extending in the peripheral direction 34, so that a proximal end 110 of the implant is released and can emerge from the outer insertion element 64*d* through the opening 155. The proximal end 110 of the implant 102 (not shown) is thus opened and positioned. At this stage, the implant 102 is still connected securely via its distal end 112 to the clamping body 10. If necessary, function tests of the implant 102 can then be carried out and the implant 102 can be removed or repositioned. The connection between the proximal end 135 of the insertion device 130*d* and the tip of the catheter 125 is ensured by the guide element 150. If the outer shaft is then withdrawn as far as the distal end 14 of the clamping body 10, the webs 26 of the clamping body 10 are released, whereby they open automatically due to their resilience and the radial force of the implant 102. The positive fit is thus released. If the clamping body is then moved further in the direction of the distal end 140 of the insertion device 130*d*, the distal end 112 of the implant 102 exits from the recess 48 and is opened due to its radial force (see FIG. 10). The tip of the catheter 125 and the part of the outer insertion element 64*d* connected thereto are then withdrawn again via the release device 100 or the clamping body 10 by means of the guide element 150, whereby the opening 155 closes again. The insertion device 130*d* can now be removed from the body. The implant 102 remains fully positioned in the body (not shown).

A distal insertion device 130 with a first alternative clamping body 10*a* is shown in FIGS. 11 to 18. The clamping body 10*a* of a release device 100 in FIGS. 11 to 18 differs from the clamping body 10 in FIGS. 1 to 8 in that a clamping effect is transferred directly to a region 104 of an implant 102 via clamping surface regions 18, 20 on the extensions 16.

Figure 11:
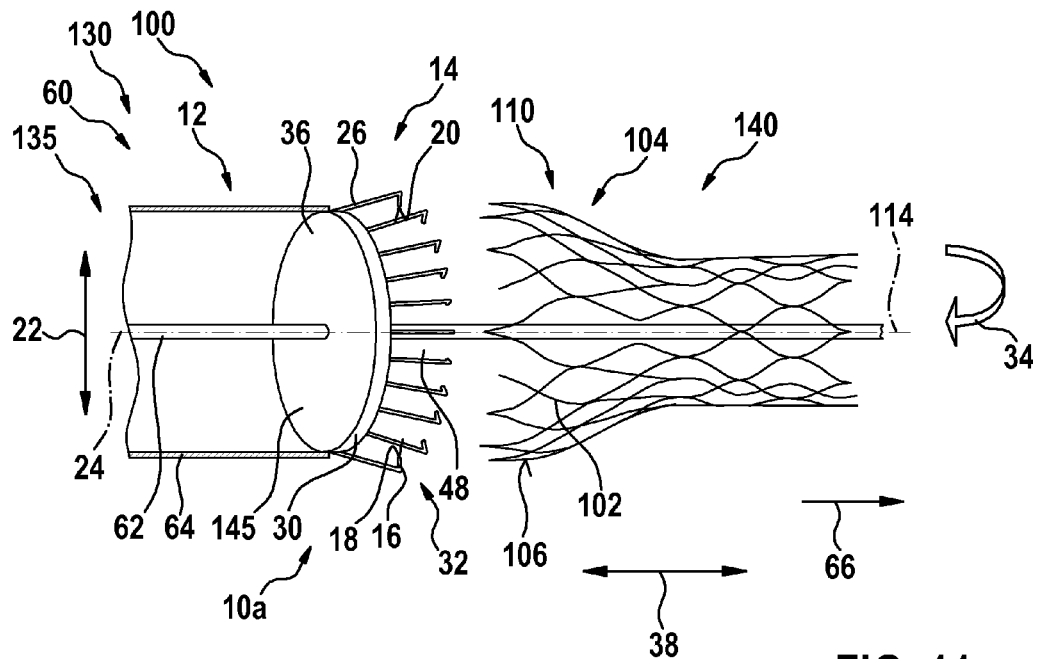
FIG. 11 shows a schematic illustration of a section through an alternative exemplary embodiment of a distal insertion device and of a release device according to the invention with a first alternative clamping body and an implant.

FIG. 11 shows a longitudinal section through the release device 100 of the distal insertion device 130, illustrated merely in part. For example, the insertion device 130 is a catheter having a shaft region 60 with two coaxially arranged insertion elements 62, 64, for example an inner shaft (insertion element 62) and an outer shaft (insertion element 64), which surrounds the inner shaft and in turn can be surrounded by an outer sleeve (not shown). The proximal end 135 of the insertion device 130 faces a user during use, that is to say as the implant 102 is fastened to the release device 100 or during implantation. The implant 102 is placed at the distal end 140 of the shaft region 60 between the inner shaft and the outer shaft and is to be released at the site of implantation in the animal or human body (see FIG. 16).

The release device 100 is used to release the medical implant 102 from the insertion device 130. The implant 102 is arranged at an end 140 of the shaft region 60 remote from the user, for example in the vicinity of the tip of a catheter 125 (see FIG. 16). For example, the implant 102 is placed around the inner insertion element 62 and is released by a relative movement between the first and the second insertion element 62, 64 beginning at a distal end 112 of the implant 102. In this case, the inner insertion element 62 is connected to the tip of the catheter 125, but by contrast the outer insertion element 64 is not.

Figure 12:
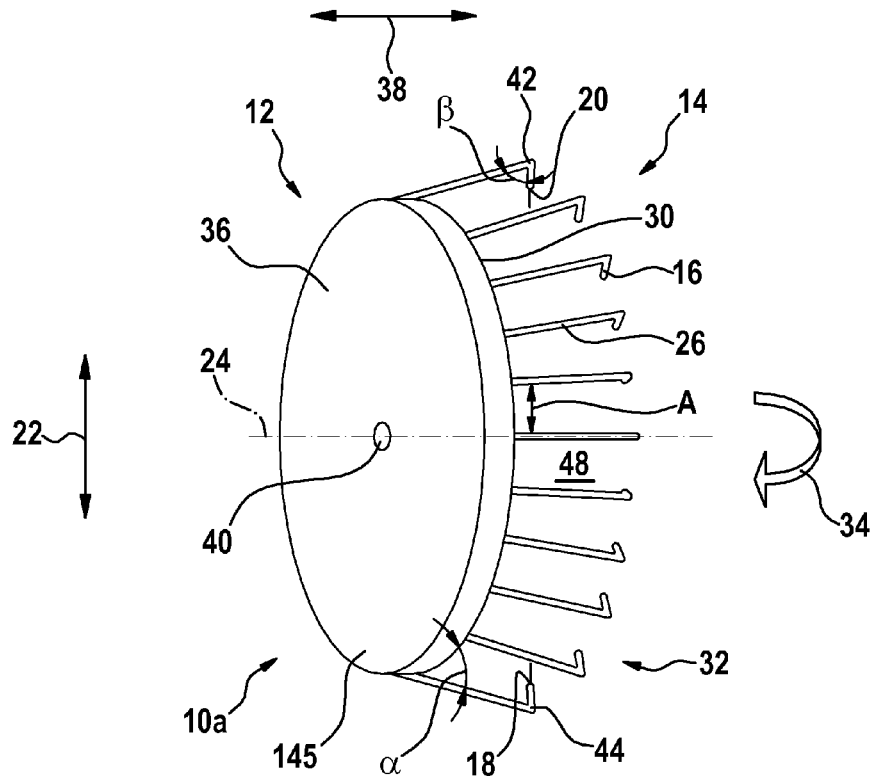
FIG. 12 shows a schematic illustration of a detail of the clamping body of the release device in FIG. 11.

The release device 100 includes the clamping body 10*a* for clamping the implant 102 in the insertion device 130. The clamping body 10*a* has a proximal end 12, which is remote from the distal end 140 of the insertion device 130 during use, and a distal end 14, which faces the distal end 140 of the insertion device 130 during use. The clamping body 10*a* is formed by a cylindrical and/or bushing-shaped element. In FIG. 12 the clamping body 10*a* is shown in a detailed illustration. A cylinder jacket 32 of the clamping body 10*a* extends in the peripheral direction 34 around an inner axis 24 of the clamping body 10 and, when assembled in the insertion device 130, around the inner insertion element 62. The cylinder jacket 32 is further composed substantially from a multiplicity of webs 26, which are distributed symmetrically or with uniform spacing A over an edge 30 or a periphery of the clamping body 10*a*. In addition, the webs 26 are arranged relative to the inner axis 24 and to the inner insertion element 62 at an angle α of substantially 30° in a neutral position of the clamping body 10*a*.

At its proximal end 12, the clamping body 10 has a base 36, which extends substantially perpendicular to the inner axis 24 of the clamping body 10*a* or, in the assembled state, substantially perpendicular to the inner insertion element 62. The webs 26 protrude from this base 36 substantially in an axial direction 38 along the inner axis 24 of the clamping body 10*a*. The clamping body 10*a* is fastened or glued to the inner insertion element 62 via this base 36. To this end, the clamping body 10*a* or the base 36 has a passage 40 for the inner insertion element 62. The fastening is achieved for example by means of a UV-curable adhesive. To limit a movement of the implant 102 in the direction of the proximal end 135 of the insertion device 130, the insertion device 130 has a stopper 145. This stopper 145 is formed by the base 36 and is thus designed integrally with the clamping body 10*a*.

Alternatively, the clamping body may have at least two radially opposed bridges instead of the base, the bridges being arranged substantially perpendicular to the inner axis of the clamping body and being fastened via their radially inner ends on the inner insertion element. In this case, the radially outer ends of the bridges would contact the cylinder jacket. This could be a ring, from which the webs protrude substantially in the axial direction (not shown).

To clamp the implant 102 in a clamping position of the clamping body 10*a*, the clamping body further has a plurality of extensions 16 and clamping surface regions 18, 20 at its distal end 14. In this case each extension 16 is arranged at an angle β of substantially 70° on a web 26, more specifically at the distal end 42 thereof. Each extension 16 is thus arranged so as to be oriented substantially in the radial direction 22 relative to the inner axis 24 of the clamping body 10*a*. The base 36, the webs 26 and the extensions 16 are formed integrally with one another or as a component. A radially inner end 44 of each extension 16 is planar or flat and forms a clamping surface region 18, 20. Each two clamping surfaces 18, 20 of radially opposed extensions 16 are arranged so as to be substantially pointing toward one another and are aligned substantially parallel to one another. In the clamped state, the two mutually opposed clamping surface regions 18, 20 clamp therebetween a region 104 of the implant 102 and thus hold the implant 102 in position.

To establish the clamped state, the clamping body 10*a* has to be transferred from its neutral position into its clamping position. To this end, the webs 26 are formed resiliently, whereby they, or their distal ends 42 with the extensions 16, can be moved radially relative to the inner axis 24. This can be achieved by a suitable material of the webs 26. In principle, it would also be conceivable to form a contact region between the base and the web in an articulated manner or with a hinged joint. Since the clamping effect is not transferred directly to the implant 102 via the webs 26 and the extensions 16, but in this case the outer insertion element 64 is required (see below for details), the clamping body 10*a* can be understood to be an indirect clamping body 10*a*.

The dimensions of the clamping body 10*a* are matched to the corresponding implant 102. An inner diameter $D_{110}$, which can be adjusted in the clamped state, of the clamping body 10 or of the radial spacing between the clamping surface regions 18, 20 is adapted to a contour or an outer diameter $D_{a102}$ of the implant 102 (see also FIG. 15). Furthermore, these parameters of the clamping body 10*a* are matched to measurements of the insertion device 130, such as an inner diameter $D_{164}$ of the insertion element 64 or of the outer shaft. In this case, an outer diameter $D_{a10}$ of the clamping body 10*a* may be the inner diameter $D_{164}$ of the outer shaft minus 0.2 mm, whereby the implant 102, when assembled in the insertion device 130, has to apply a radial force sufficient to push the clamping body 10 or the webs 26 radially in the direction of the outer shaft by 0.1 mm. The inner diameter $D_{110}$, which can be adjusted in the clamped state, for example equals the outer diameter $D_{a10}$ of the clamping body 10 minus twice a height H of the extension 16.

Figure 13:
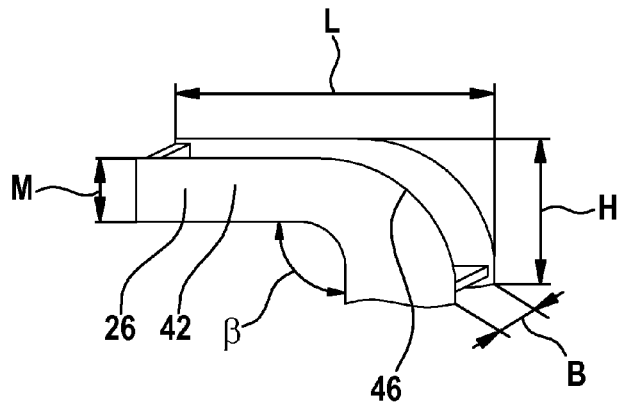
FIG. 13 shows a schematic illustration of a detail of a web with extension of the clamping body from FIG. 11.

FIG. 13 shows a web 26 and an extension 16 in detail. A length L of the web 26 is 5 mm to 15 mm for example, wherein the base 36 may have a length of approximately 5 mm. The height H of the extension 16 is 1 mm to 2 mm for example, and a width B of the extension 16 and of the web 26 is 1 mm to 2 mm for example. In this case, it must be taken into account that the width B is greater than a width of a recess 108, which for example is rhombic, in the implant 102 (see FIGS. 11, 14, 15 and 16, not illustrated to scale). A material thickness M of the web is 0.1 mm to 0.2 mm for example. Transition regions from the web 26 to the extension 16 are designed with rounded portions 46 to protect an inner surface of the insertion element 64. The clamping body 10*a* is for example made of a hard monolayer design polymer (for example polyamide TR55LX from EMS Chemie) with high friction so as to hold the implant 102 in position in the clamped state.

In principle, the clamping body can also be formed from a radiopaque metal, such as stainless steel, tantalum, gold or platinum. A progression of the inner insertion element, and therefore of the implant, as well as a correct position of the implant at a site of implantation could thus be monitored with use of an x-ray device (not shown here) during implantation of the implant by means of the insertion device.

Figure 14:
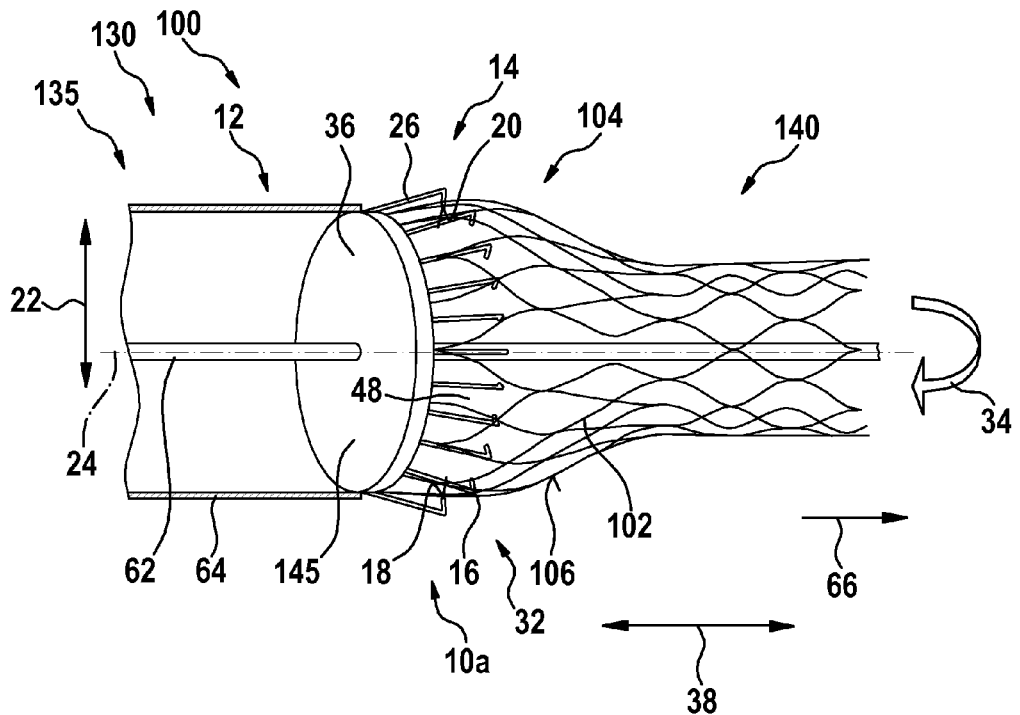
Figure 15:
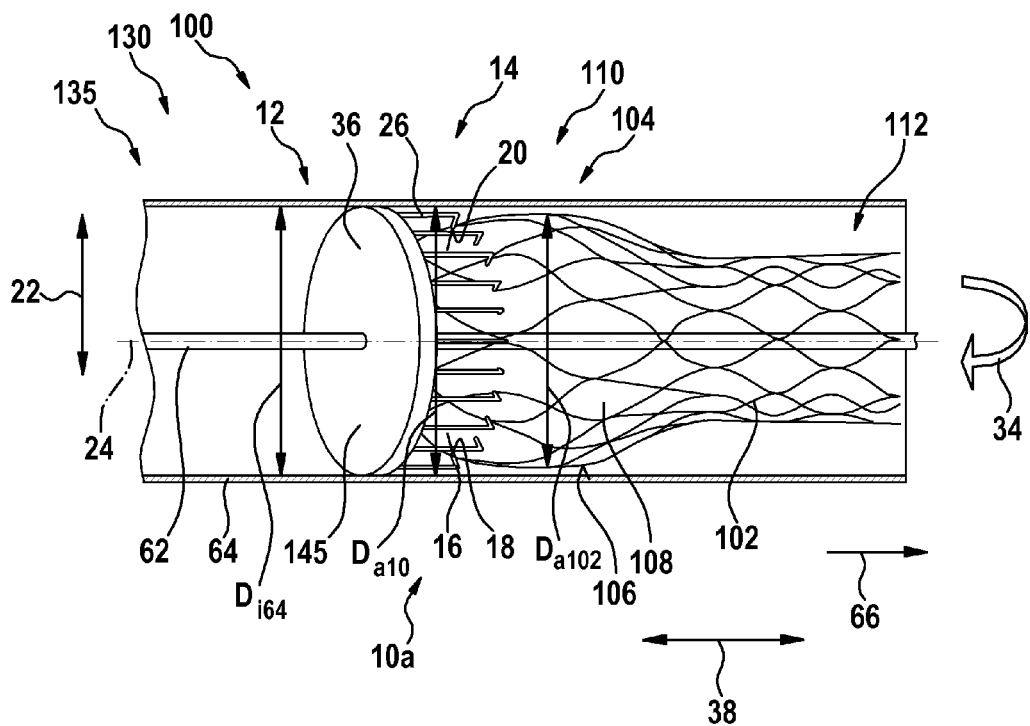

FIG. 11 shows the clamping body 10*a* arranged in the insertion device 130 before placement of the implant 102. In this case, the outer insertion element 64 is withdrawn in the direction of the proximal end 135 of the insertion device 130 as far as the axial position of the base 36 of the clamping body 10*a*. No clamping force is exerted on the webs 26 and the clamping body 10*a* is in its neutral position. In this open position, the clamping body 10*a* is ready for use and for receipt of the implant 102. The placement of the implant 102 in the opened clamping body 10*a* is shown in FIG. 14. The implant 102, for example a stent or an artificial cardiac valve implant, is self-expanding and is formed with no fastening elements. A method for clamping the implant 102 by means of the clamping body 10*a* is described hereinafter with reference to FIGS. 14 to 18.

In this case, the region 104 or a proximal end 110 of the implant 102, which is crimped onto the inner shaft, is introduced with the inner shaft into a receptacle 48 of the cylinder jacket 32 of the clamping body 10*a* in a first step. This occurs from the direction of the open or distal end 14 of the clamping body 10*a*. The sliding movement takes place for example until the proximal end 110 of the implant 102 contacts the stopper 145. The stopper 145 thus limits the movement of the implant 102 in the direction of the proximal end 135 of the insertion device 130. The implant 102 is then placed such that the region 104 is arranged radially between the clamping surface regions 18, 20 of the extensions of the clamping body 10*a* (see FIG. 14).

Figure 16:
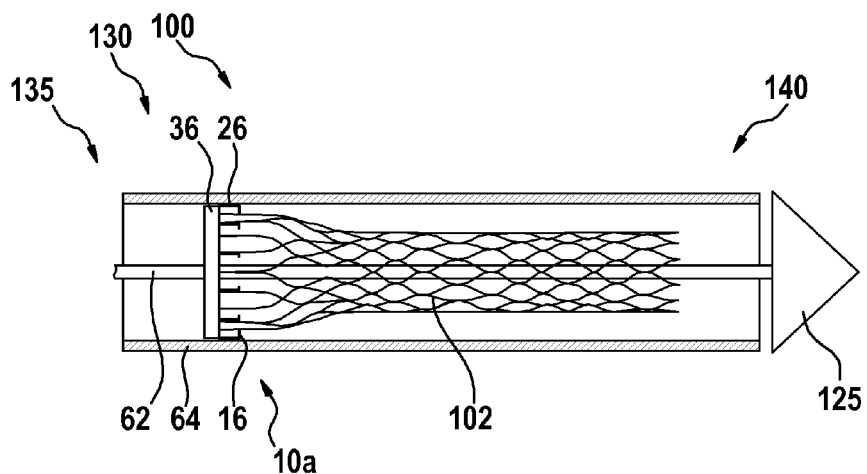
FIG. 16 shows a schematic illustration from the side of the insertion device and the clamping body from FIG. 15.
Figure 17:
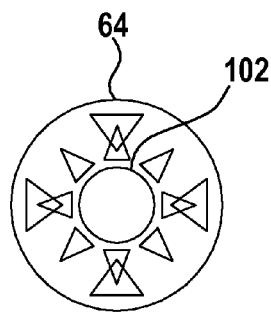
FIG. 17 shows a schematic illustration of the insertion device and the clamping body from FIG. 11 with the implant fully released.
Figure 18:
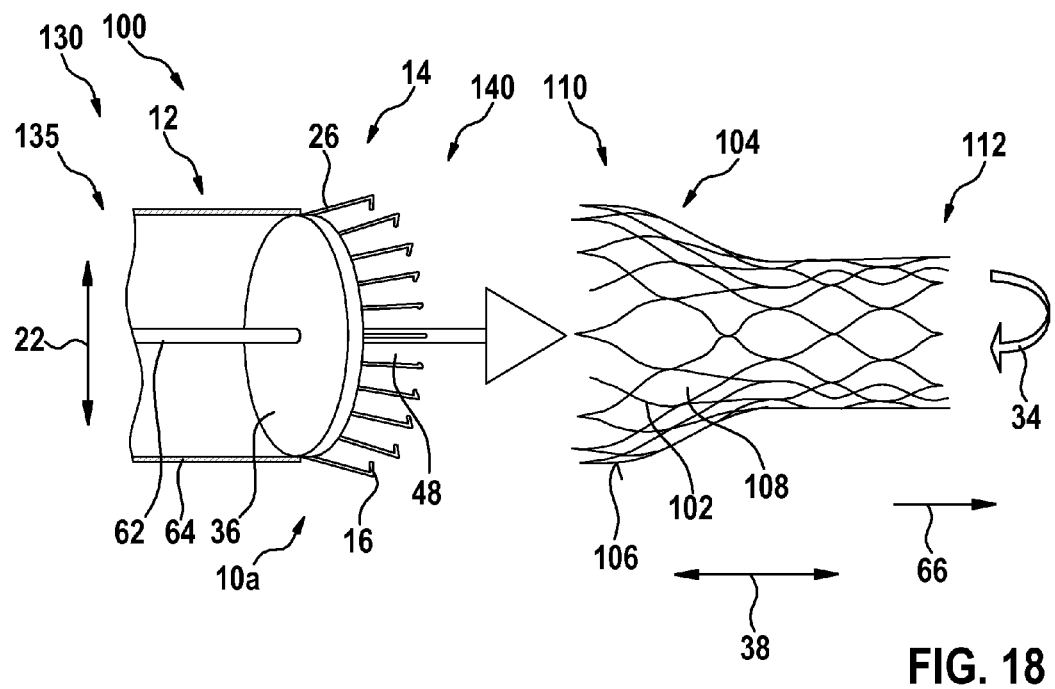
FIG. 18 shows a schematic illustration of holding forces of the insertion device, of the clamping body and of the implant.

In a subsequent, second step the clamping body 10*a* together with the implant 102 is placed in the outer insertion element 64. This occurs by moving the outer insertion element 64 in the direction of the distal end 140 of the insertion device 130. The webs 26 are thus pushed radially inwardly due to their spring property and the proximal end 110 of the implant 102 is thus surrounded by the webs 26 or the clamping surface regions 18, 20. As the implant 102 is surrounded by the clamping surface regions 18, 20 of the clamping body 10*a*, it is pressed together and the region 104 is clamped radially between the clamping surface regions 16, 18. In this clamped state, the extensions 16 abut an outer face 106 of the region 104 of the implant 102 via their respective clamping surface region 18, 20, wherein the outer face 106 extends substantially parallel to an inner axis 114 of the implant 102. In addition, in the clamped state the webs 26 extend in the axial direction 38 parallel to the inner axis 24 or to the inner insertion element 62 and are arranged in the peripheral direction 34 around the proximal end 110 of the implant 102. The extensions 16 are then arranged substantially perpendicular to the inner axis 24 or to the inner insertion element 62 (see FIG. 15). The clamping body 10a is thus placed together with the implant 102 in the outer insertion element 64 and assembly is complete. This is also shown in FIG. 16, which shows a schematic side view of the insertion device 130 with the clamping body 10a in its clamped position and the implant 102 placed in position.

In the clamped state, interaction between a holding force of an insertion element 64 and a radial force of the implant 102 holds the clamping body 10a and the implant 102 in position. The holding force and the radial force are illustrated schematically in FIG. 17 by means of the mutually opposed triangles (the clamping body 10a and the inner insertion element 62 are not shown in this case). In addition, the clamping body 10a has a high static friction due to its material properties. As a result of the static friction between the clamping body 10a and the implant 102, the clamping body 10a has a holding force that additionally holds the implant 102 in position in the insertion device 130 in the clamped state, whereby the implant 102 is prevented from sliding out. The following definition can be given for the static friction $F_H$: $F_H = \mu_H \cdot F_N$ where: $\mu L_H$: static friction coefficient (material-dependent coefficient, material of the clamping body 10a and/or of the implant 102) of the clamping surface regions 18, 20 and the outer surface 106, $F_N$: nominal force, resulting from the radial force of the insertion element 64 (with reaction of the radial force of the implant 102). In the clamped state, interaction between the holding force of the insertion element 64 and the holding force of the clamping body 10a thus holds the implant 102 in position.

For implantation of the implant 102 in the body, the insertion device 130 thus prepared is introduced into the body (not shown) in a direction of insertion 66. Due to the movement of the outer insertion element 64 in the direction of the proximal end 135 of the insertion device 130, the distal end 112 of the implant 102 is released, the implant opening and being positioned due to its ability to self-expand (not shown). At this stage, the implant 102 is still connected securely via its proximal end 110 to the clamping body 10a. If necessary, function tests of the implant 102 can then be carried out. If a malfunction is established, the implant 102 can be removed again from the body. Repositioning of an incorrectly positioned implant 102 is also possible. If the outer shaft is then withdrawn as far as the stopper 145 or base 36, the webs 26 of the clamping body 10 are released, whereby they open automatically due to their resilience and the radial force of the implant 102. The proximal end 110 of the implant 102 is thus also released and opened due to its radial force. The clamping body 10 is thus moved by the resilience of the webs 26 into the neutral position to release the region 104 of the implant 102 (see FIG. 18). The release device 100 or the clamping body 10a is then withdrawn with the inner shaft into the outer shaft, whereby the clamping body 10a is compressed again, and the insertion device 130 is removed from the body. The implant 102 remains fully positioned in the body (not shown).

Figure 19A:
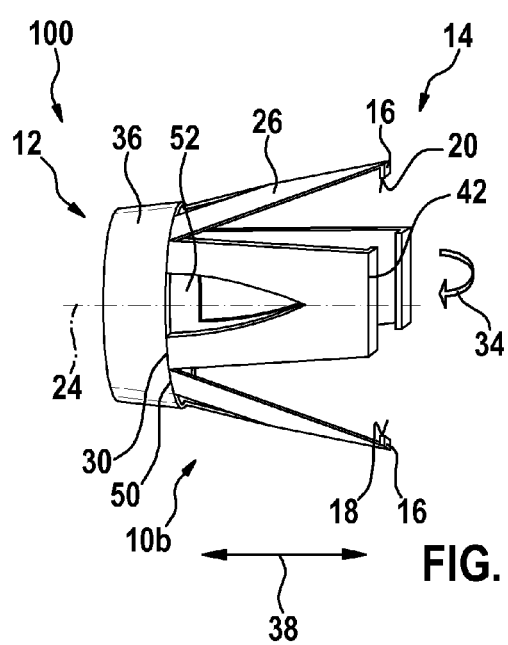
FIG. 19A shows a schematic side illustration of a second alternative clamping body.
Figure 19B:
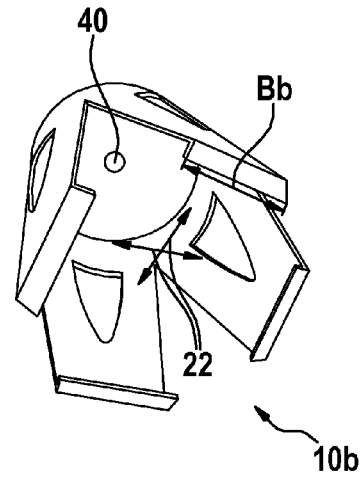
FIG. 19B shows a schematic perspective illustration of the clamping body of FIG. 19A.

A clamping body 10b of a release device 100 of FIGS. 19A and 19B differs from the clamping body 10a of FIGS. 11 to 18 in that it has four webs 26, which are distributed symmetrically over an edge 30 or a periphery of the clamping body 10b. A width $B_b$ of the extensions 16 extending radially relative to an inner axis 24 is wider than the width B of the extensions 16 in the exemplary embodiment of FIGS. 11 to 18 (see FIG. 19B) due to the reduced number of webs 26. In addition, the webs 26 taper conically from their point of contact 50 with a base 36 toward their distal end 42. To reduce the weight of the clamping body 10a, the webs 26 have triangular recesses 52.

Figure 20:
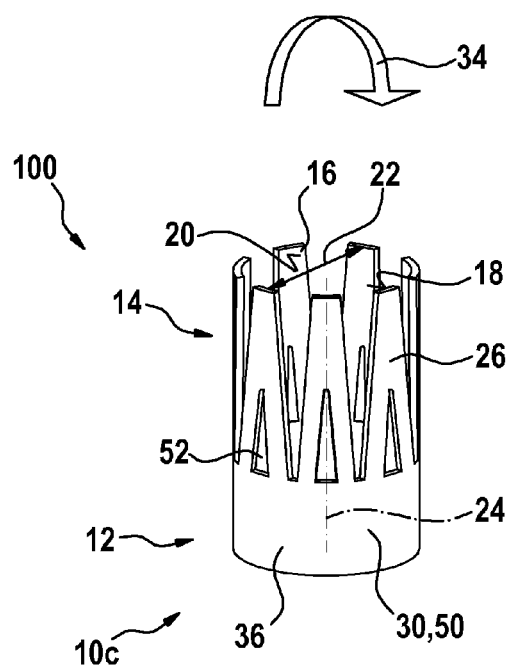
FIG. 20 shows a schematic side illustration of a third alternative clamping body.

A clamping body 10c of a release device 100 in FIG. 20 differs from the clamping body 10a in FIGS. 11 to 18 and from that in FIGS. 19A and 19B in that the clamping body 10c has six webs 26 and is made from spring steel.

Figure 21:
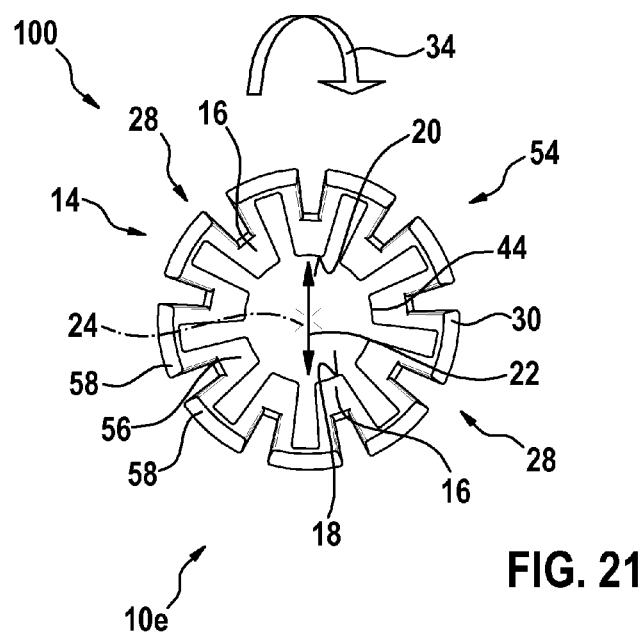
FIG. 21 shows a schematic front illustration of a fourth alternative clamping body.

A clamping body 10e of a release device 100 of FIG. 21 differs from the clamping body 10a of FIGS. 11 to 18 in that the clamping body 10e is formed by a ring 54 made of spring steel having a plurality of ring segments 28, which are arranged in succession in the peripheral direction 34, distributed symmetrically over an edge 30 of the clamping body 10e. In this case, a ring segment 28 includes a depression 56, which points in the radial direction 22 toward the inner axis 24 of the clamping body 10e and is flanked by two elevations 58. The clamping body 10e thus has a ring 54 with an undulation running in the peripheral direction 34. Each depression 56 constitutes an extension 16, at the radial inner end 44 of which a planar or flat clamping surface region 18, 20 is formed. Each two clamping surfaces 18, 20 of substantially radially opposed extensions 16 are arranged substantially facing one another and are aligned substantially parallel to one another. The extensions 16 are formed resiliently, more specifically in a direction perpendicular to the drawing plane. In the clamped state, the two mutually opposed clamping surface regions 18, 20 can thus clamp therebetween a region of an implant (not shown in this case) and can thus hold the implant in position. The ring 54 is arranged or fastened to fasten the clamping body 10e on an inner insertion element (not shown in this case) via a cylinder jacket (not shown here in greater detail) extending perpendicular to the drawing plane, the cylinder jacket having a base.

FIG. 22 shows a longitudinal section through an exemplary embodiment of a release device 100 of an alternative proximal insertion device 130d, illustrated merely in part. For example, the insertion device 130d is a catheter having a shaft region 60 with two coaxially arranged insertion elements 62d, 64d, for example an inner shaft (insertion element 62d) and an outer shaft (insertion element 64d), which surrounds the inner shaft and in turn can be surrounded by an outer sleeve (not shown). The proximal end 135 of the insertion device 130d faces a user during use, that is to say as the implant 102 is fastened to the release device 100 or during implantation. The implant 102 is placed at the distal end 140 of the shaft region 60 between the inner shaft and the outer shaft and is to be released at the site of implantation in the animal or human body. For example, the implant 102 is placed around the inner insertion element 62d and is released by a relative movement between the first and second insertion element 62d, 64d beginning at a proximal end 110 of the implant 102. In this case the outer insertion element 64d is connected to the tip of the catheter 125, but by contrast the inner insertion element 62d is not. To connect the proximal end 135 of the insertion device 130d and the tip of the catheter 125, the guide device 130d has a guide element 150, which runs coaxially with the inner insertion element 62d and therein and is formed for example by a shaft having an insertion wire and a lumen. The release device 100 includes a clamping body 10a, formed similarly to the clamping body 10a of FIGS. 11 to 18, for clamping the implant 102 in the insertion device 130d. Compared to the exemplary embodiment in FIGS. 11 to 18 however, the clamping body 10a is in this case arranged on the inner insertion element 62d, turned through 180°.

A method for connecting the implant 102 by means of the clamping body 10a and therefore by means of the proximal insertion device 130d will now be described with reference to FIGS. 22 and 23. In a first step, the previously cooled, crimped implant 102 is placed on the inner insertion element 62d. In this case, the region 104 of the implant 102 is slid over the inner insertion element 62d into the receptacle 48 of the clamping body 10a. The sliding movement is carried out for example until the distal end 112 of the implant 102 or of the region 104 contacts the stopper 145 (not shown). The stopper 145 thus limits the movement of the implant 102 in the direction of the distal end 140 of the insertion device 130d.

Alternatively, it would also be possible to place the implant 102 on the insertion element 62d in the direction of the proximal end 135 of the insertion device 130d. In this case, the entire implant 102 is slid over the tip of a catheter 125 and over the inner insertion element 62d. In this case, the clamping body 10a would only be applied and fastened to the inner insertion element 62d once the implant 102 had been placed in position.

In a second step, the outer insertion element 64d is slid on in the direction of the proximal end 135 of the insertion device 130d, whereby the clamping body 10a is pressed together or the webs 26 thereof are pressed radially inwardly. The region 104 of the implant 102 is hereby pressed together by the abutment of clamping surface regions 18, 20 of the clamping body 10a, and the region 104 is clamped radially between the clamping surface regions 16, 18. The clamping body 10a together with the implant 102 is placed in the outer insertion element 64d and assembly is complete (see FIG. 22).

For implantation of the implant 102 in the body, the insertion device 130d thus prepared is introduced into the body in a direction of insertion 66. Due to the movement of the tip of the catheter 125 and of the outer insertion element 64d in the direction of the distal end 140 of the insertion device 130d by means of the guide element 150, an opening 155 is released at the outer insertion element 64d, the opening extending in the peripheral direction 34, so that a proximal end 110 of the implant 102 is released and can emerge from the outer insertion element 64d through the opening 155. The proximal end 110 of the implant 102 (not shown) is thus opened and positioned. At this stage, the implant 102 is still connected securely via its distal end 112 to the clamping body 10a. If necessary, function tests of the implant 102 can then be carried out and the implant 102 can be removed or repositioned. The connection between the proximal end 135 of the insertion device 130d and the tip of the catheter 125 is ensured by the guide element 150. If the outer shaft is then withdrawn as far as the stopper 145 or base 36, the webs 26 of the clamping body 10a are released, whereby they open automatically due to their resilience and the radial force of the implant 102. The distal end 112 of the implant 102 is thus also opened due to its radial force (see FIG. 23). The tip of the catheter 125 and the part of the outer insertion element 64d connected thereto are then withdrawn again via the release device 100 or the clamping body 10a by means of the guide element 150, whereby the opening 155 closes again. The insertion device 130d can now be removed from the body. The implant 102 remains fully positioned in the body (not shown).

It will be apparent to those skilled in the art that numerous modifications and variations of the described examples and embodiments are possible in light of the above teaching. The disclosed examples and embodiments are presented for purposes of illustration only. Other alternate embodiments may include some or all of the features disclosed herein. Therefore, it is the intent to cover all such modifications and alternate embodiments as may come within the true scope of this invention.

What is claimed is:

1. A release device with an engaged medical implant, wherein the medical implant is held within an insertion device and the release device is configured to release the implant from the insertion device by a relative movement between a first and a second insertion element of the insertion device, the release device comprising a clamping body clamped to the implant, the clamping body comprising:
 a proximal end, which is remote from a distal end of the insertion device during use, and comprising a distal end, which faces the distal end of the insertion device during use;
 a cylinder spaced outside of and extending around an inner surface to form a receptacle for receiving the implant between the cylinder and the inner surface, wherein the cylinder comprises an engagement element through which the received implant is engaged; and
 at least one web comprising at its distal end an extension oriented substantially in a radial direction relative to an inner axis of the clamping body, the extension engaging the received implant through the engagement element and within the receptacle to provide a clamped state.

2. The release device as claimed in claim 1, wherein the at least one web and/or the extension is formed resiliently.

3. The release device as claimed in claim 2, wherein the clamping body has a multiplicity of webs, which are distributed symmetrically over a peripheral edge of the clamping body.

4. The release device as claimed in claim 1, wherein the at least one web can be arranged relative to the inner axis of the clamping body at an angle ($\alpha$) of substantially 30°, and/or wherein the extension is arranged on the at least one web at an angle ($\beta$) of substantially 70°.

5. The release device as claimed in claim 1, wherein the clamping body has a holding position in the clamped state and, when the holding position is released, has a neutral position, wherein the clamping body is movable into the neutral position by a resilience of the at least one web and/or the extension so as to release the implant.

6. The release device as claimed in claim 1, wherein the receptacle comprises a slit to receive the implant, wherein the slit extends at least along part of an edge of the clamping body.

7. The release device as claimed in claim 1, wherein the receptacle has at least one separating structure, which divides the receptacle into at least two receptacle sectors and/or which fixes the implant in the receptacle in a direction along an edge of the clamping body, at least in an intended insertion state.

8. The release device as claimed in claim 1, wherein the clamping body has at least one insertion aid, which is designed to guide insertion of the implant and which is arranged before the receptacle of the clamping body in a direction of supply when introducing the implant into the clamping body.

9. The release device as claimed in claim 1, wherein the clamping body is configured to be fastened to one of the insertion elements, in particular via its proximal end or its distal end.

10. The insertion device as claimed in claim 1, wherein the engagement element is an aperture sized to accept the extension and permits access to the received implant through the aperture.

11. An insertion device for insertion of a medical implant, which can be released by a relative movement between a first and a second insertion element, the insertion device comprising a release device engaged with the medical implant and for releasing the medical implant, the release device comprising an indirect and/or direct clamping body clamped to the implant in the insertion device, the clamping body comprising:

a proximal end, which is remote from a distal end of the insertion device during use, and comprising a distal end, which faces the distal end of the insertion device during use;

a cylinder spaced outside of and extending around an inner surface to form a receptacle for receiving the implant between the cylinder and the inner surface, wherein the outer cylinder comprises an engagement element through which the received implant is capable of engagement; and at least one web comprising at its distal end an extension oriented substantially in the radial direction relative to an inner axis of the clamping body, the extension engaging the received implant through the engagement element and within the receptacle to provide a clamped state.

12. The insertion device as claimed in claim 11, wherein a stopper is provided, which limits a movement of the implant in the direction of a proximal end of the insertion device or in the direction of the distal end of the insertion device, wherein the clamping body is formed integrally with the stopper.

13. The insertion device as claimed in claim 11, wherein the implant is a self-expanding implant and/or has no fastening elements.

* * * * *